(12) United States Patent
Singer et al.

(10) Patent No.: US 6,323,337 B1
(45) Date of Patent: Nov. 27, 2001

(54) QUENCHING OLIGONUCLEOTIDES

(75) Inventors: Victoria L. Singer; Richard P. Haugland, both of Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 0 days.

(21) Appl. No.: 09/570,343

(22) Filed: May 12, 2000

(51) Int. Cl.$^7$ .................................................. C07H 21/04
(52) U.S. Cl. ................................ 536/26.6; 435/6
(58) Field of Search ................................ 435/6; 536/26.6

(56) References Cited

U.S. PATENT DOCUMENTS

| | | |
|---|---|---|
| 4,258,118 | 3/1981 | Foley . |
| 4,318,846 | 3/1982 | Khanna . |
| 4,774,339 | 9/1988 | Haugland . |
| 4,810,636 | 3/1989 | Corey . |
| 4,812,409 | 3/1989 | Babb . |
| 4,883,867 | 11/1989 | Lee . |
| 4,945,171 | 7/1990 | Haugland . |
| 5,187,288 | 2/1993 | Kang . |
| 5,227,487 | 7/1993 | Haugland . |
| 5,248,782 | 9/1993 | Haugland . |
| 5,274,113 | 12/1993 | Kang . |
| 5,321,130 | 6/1994 | Yue . |
| 5,410,030 | 4/1995 | Yue . |
| 5,433,896 | 7/1995 | Kang . |
| 5,436,134 | 7/1995 | Haugland . |
| 5,491,063 | 2/1996 | Fisher et al. . |
| 5,582,977 | 12/1996 | Yue . |
| 5,658,751 | 8/1997 | Yue . |
| 5,691,145 | 11/1997 | Pitner et al. . |
| 5,696,157 | 12/1997 | Wang . |
| 5,714,327 | 2/1998 | Houthoff . |
| 5,763,181 | 6/1998 | Han et al. . |
| 5,804,386 | 9/1998 | Ju . |
| 5,830,912 | 11/1998 | Gee . |
| 5,846,726 | 12/1998 | Nadeau . |
| 5,863,753 | 1/1999 | Haugland . |
| 6,005,113 | 12/1999 | Wu . |
| 6,013,442 | 1/2000 | Kolesar et al. . |
| 6,027,923 | 2/2000 | Wallace . |

FOREIGN PATENT DOCUMENTS

| | | |
|---|---|---|
| 24 60 491 | 7/1976 | (DE) . |
| 0 745 690 A2 | 12/1996 | (EP) . |
| WO 97/39064 | 10/1997 | (WO) . |
| WO 99/11813 | 3/1999 | (WO) . |
| WO 99/15517 | 4/1999 | (WO) . |
| WO 99/28500 | 6/1999 | (WO) . |
| WO 99/37717 | 7/1999 | (WO) . |

OTHER PUBLICATIONS

R. Haugland, Molecular Probes Handbook of Fluorescent Probes and Research Chemicals, Chapters 1–3 (1996).
R. Haugland Molecular Probes Handbook of Fluorescent Probes and Research Chemicals, Sixth Edition, Chapter 19 (1996).
Bioprobes 26 (Oct. 1997).
Bioprobes 27 (Feb. 1998).
Bioprobes 28 (May. 1998).
Bioprobes 29 (Nov. 1998).
Bioprobes 30 (Jan. 1999).
Bioprobes 31 (May 1999).
Bioprobes 32 (Dec. 1999).
Bioprobes 33 (Feb. 2000).
Bioprobes 34 (May 2000).
Wang, et al, *Antiviral Chemistry 7 Chemotherapy* 8, 303 (1997).
Tyagi et al., Nature Biotechnology 16, 49 (1998).
Proceedings of the National Academy of Science, USA 89, 392 (1992).
Proceedings of the National Academy of Science, USA 88, 189 (1991.
Nature 350, 91 (1991).
Proceedings of the National Academy of Science, USA 87, 1874 (1990).
R. Haugland Molecular Probes Handbook of Fluorescent Probes and Research Chemicals, Seventh Edition CD–ROM, (1999).

*Primary Examiner*—Scott W. Houtteman
(74) *Attorney, Agent, or Firm*—Allegra J. Helfenstein; Anton E. Skaugset

(57) ABSTRACT

The invention relates to oligonucleotides labeled with an energy transfer acceptor useful in conjunction with fluorescent nucleic acid stains. The resulting oligonucleotides are useful for decreasing background fluorescence during amplification assays and in ligation assays, and for detecting hybridization.

64 Claims, 4 Drawing Sheets

10-mer 30-mer 100-mer

Figure 2
Fig. 2A
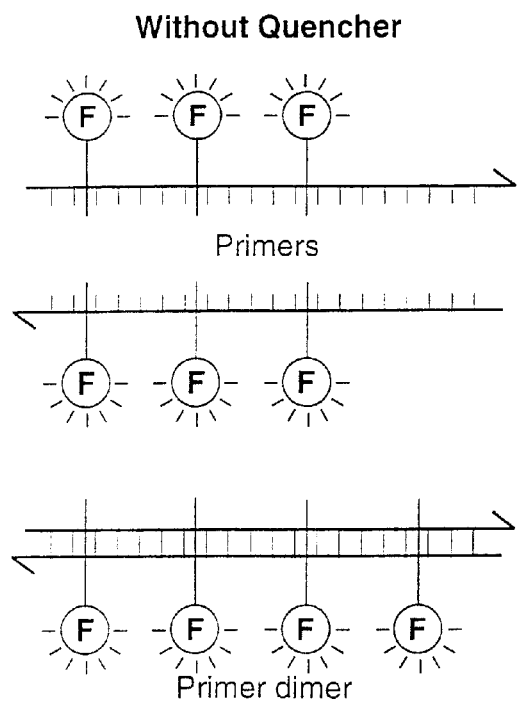
Without Quencher
Fig. 2B
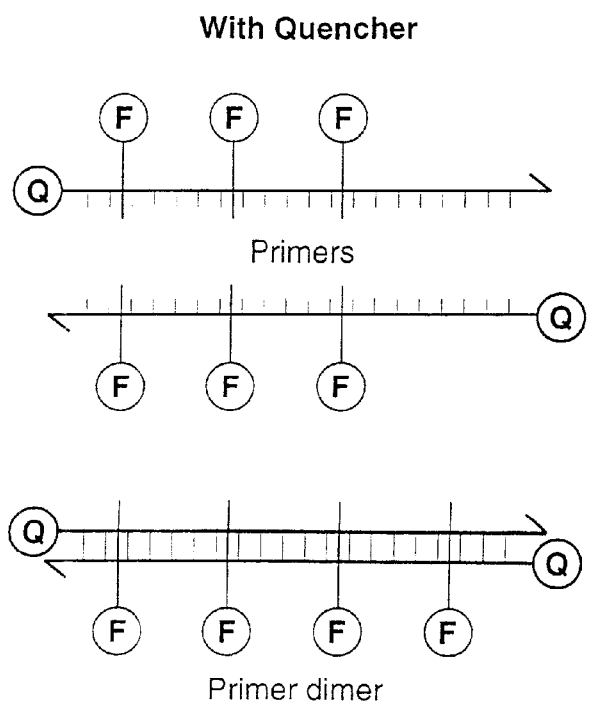
With Quencher

Figure 3

Starting Materials

Original template

Leftward primer

Rightward primer

First round amplification

Second round amplification

Subsequent amplification

QUENCHING OLIGONUCLEOTIDES

FIELD OF THE INVENTION

The invention relates to oligonucleotides labeled with dyes that are capable of accepting transfer of energy from associated luminescent nucleic acid stains. The use of these oligonucleotides decreases the background fluorescence due to luminescent staining of oligonucleotides in amplification assays, elongation assays, or enzyme assays.

BACKGROUND

Luminescent nucleic acid stains are molecules that non-covalently associate with oligonucleotides or nucleic acids, and are either intrinsically luminescent (typically fluorescent) or that display a change in their spectral characteristics upon associating with ox nucleic acids. The rapid development of new fluorescent nucleic acid stains has resulted in the use of fluorescence-based methods in a wide variety of studies directed at or using nucleic acids.

Typically the addition of a nucleic acid stain results in the fluorescent staining of most or all nucleic acid fragments present in the sample. The resulting undifferentiated staining often limits the utility of nucleic acid stains in some assays, or necessitates additional separation steps either before or after staining.

However, when some of the nucleic acid fragments (e.g. oligonucleotides) are covalently labeled with a quenching moiety, the fluorescence intensity of the associated nucleic acid stain molecules in the vicinity is decreased or even fully quenched. The quenching moiety may emit fluorescence at a wavelength longer than that of the nucleic acid stain, it may be dimly fluorescent, or essentially nonfluorescent.

Energy transfer pairs where both the donor and acceptor are covalently bound to the same nucleic acid are known. Such energy transfer pairs have been used to detect changes in oligonucleotide conformation, such as in Tyagi et al. (EP 0 745 690 A2 (1996)) and Pitner et al. (U.S. Pat. No. 5,691,145 (1997)). They also have been used to detect cleavage of the oligonucleotide at a point between the donor and acceptor dyes, such as in Han et al. (U.S. Pat. No. 5,763,181 (1998)), Nadeau et al. (U.S. Pat. No. 5,846,726 (1998)), and Wang et al. (ANTIVIRAL CHEMISTRY & CHEMOTHERAPY 8, 303 (1997)). Energy transfer pairs covalently bound to oligonucleotides have also been used to provide a shift in the ultimate emission wavelength upon excitation of the donor dye, such as by Ju (U.S. Pat. No. 5,804,386 (1998)).

The combination of a non-covalently bound nucleic acid stain with a covalently attached fluorophore on a single-stranded oligonucleotide hybridization probe has been used to detect specific DNA target sequences by monitoring the fluorescence of either the nucleic acid stain or the covalent label, such as in Lee and Fuerst (PCT Int. Appl. WO 99 28,500).

However, the use of a covalently bound acceptor moiety to decrease the fluorescence of noncovalently associated fluorescent nucleic acid stains has not previously been described. In addition, the use of an essentially nonfluorescent, covalently bound acceptor dye for the purpose of quenching the fluorescence of multiple fluorescent nucleic acid stain molecules bound at the same time to the same oligonucleotide has not been previously described, particularly where the oligonucleotide is a primer for a nucleic acid amplification or elongation reaction.

The methods of the present invention permit a significant reduction in background fluorescence levels where fluorescent nucleic acid stains are used in assays that require the presence of large numbers of oligonucleotide primers. In particular, the contribution to total fluorescence due to nucleic acid stains associated with primers, or primer dimers, can be substantially reduced or essentially eliminated. The reagents and methods described herein also permit continuous assays of chain elongation that do not require reagent addition or separation steps.

BRIEF DESCRIPTION OF THE DRAWINGS

FIG. 2: A qualitative depiction of fluorescent nucleic acid stains (F) on oligonucleotide primers and a primer dimer in the absence of a covalently bound quenching moiety (Q) (FIG. 2A) and the quenching of fluorescence in the presence of a covalently bound quenching moiety (Q) (FIG. 2B).

FIG. 3: A depiction of the components present during PCR amplification of a target strand.

SUMMARY OF THE INVENTION AND DESCRIPTION OF THE PREFERRED EMBODIMENTS

Figure 1:
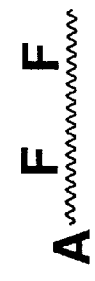
FIG. 1: A qualitative depiction of the quenching of fluorescent nucleic acid stains (F) on an oligonucleotide when they are in sufficient proximity to a quenching moiety (A). While the fluorescence of a stained 10-mer is essentially completely quenched, the fluorescence of a stained 30-mer is only partially quenched, and the fluorescence of a stained 100-mer is only slightly quenched.
Figure 1:
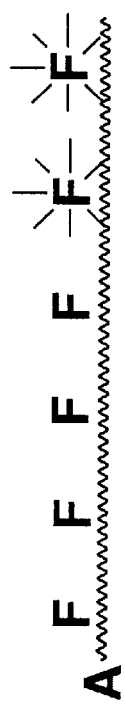
Figure 1:
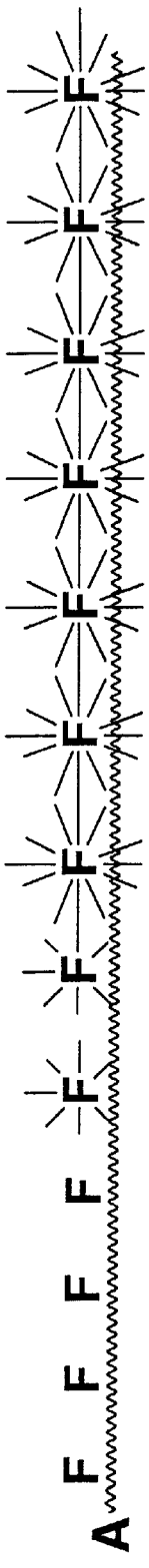

The instant invention relates to the use of dye-labeled oligonucleotides that detectably quench the luminescence of non-covalently bound nucleic acid stains. In one aspect, the invention comprises an oligonucleotide that is covalently bound to at least one quenching moiety, and also non-covalently associated with one or more fluorescent nucleic acid stains. The invention also relates to a method of detecting the amplification of a target nucleic acid that reduces background fluorescence. The invention also relates to a method of detection elongation of a nucleic acid that reduces background fluorescence. In yet another aspect, the invention relates to an assay for an enzyme that is a ligase or a nuclease enzyme. The invention also relates to oligonucleotides that are covalently labeled with a quenching moiety, and noncovalently labeled with luminescent nucleic acid stains, wherein energy transfer from the nucleic acid stains to the quenching moiety occurs. The invention also relates to kits that incorporate the quenching moiety-labeled oligonucleotides described herein and a nucleic acid stain.

The quenching oligonucleotides used in the practice of the methods of the invention possess utility for decreasing background fluorescence. This background fluorescence is typically due to the binding of nucleic acid stains to oligonucleotide primers used in primer extension, reverse transcription, DNA polymerization, RNA polymerization and other primed strand elongation processes. The quenched oligonucleotides are particularly usefil for reducing background fluorescence due to the staining of primer dimers present during amplification assays.

The quenching ohgonucleotides described herein are also useful for decreasing the fluorescence background in enzyme assays, by reducing the fluorescence that would otherwise arise from binding of nucleic acid stains to ligase substrates, or nuclease substrates.

Oligonucleotides

Preferred oligonucleotides are single-stranded, natural or synthetic DNA or RNA oligonucleotides that optionally incorporate an unusual linker such as morpholine-derivatized phosphates (AntiVirals, Inc., Corvallis Oreg.), or peptide nucleic acids such as N-(2-aminoethyl)glycine units, where the oligonucleotide contains about 6–100 bases. In another embodiment, the oligonucleotide contains about 6–60 bases. In yet another embodiment, the oligonucleotide contains less than about 30 bases.

In a preferred embodiment, the oligonucleotide is a primer useful for the amplification of a nucleic acid template by the polymerase chain reaction (PCR), real-time/kinetic PCR, reverse transcription PCR (RT PCR), linked linear amplification (U.S. Pat. No. 6,027,923 to Wallace (2000), incorporated by reference), the strand displacement assay (SDA, PROCEEDINGS OF THE NATIONAL ACADEMY OF SCIENCE, USA 89, 392 (1992), incorporated by reference), the ligase chain reaction (LCR, PROCEEDINGS OF THE NATIONAL ACADEMY OF SCIENCE, USA 88, 189 (1991), incorporated by reference), nucleic acid sequence-based amplification (NASBA, NATURE 350, 91 (1991), incorporated by reference), Q beta replicase-based amplification, cycling probe reaction CPR), solid phase amplification (SPA), self-sustained sequence replication (3SR, PROCEEDINGS OF THE NATIONAL ACADEMY OF SCIENCE, USA 87, 1874 (1990), incorporated by reference), terminal transferase-based elongation, or telomerase assays.

In one aspect of the invention, the quenching oligonucleotide optionally further comprises a second oligonucleotide that is hybridized to the quenching oligonucleotide. By hybridization is meant that the two oligonucleotide sequences form a stable double-stranded structure by hydrogen bonding between bases in the two sequences. A stable hybrid may be formed even though the two sequences are not completely complementary, if the sequences include regions of sufficient complementarity that the resulting hybrid is stable under standard laboratory conditions. The second oligonucleotide is optionally covalently labeled with a quenching moiety, which may be the same as or different from the quenching moiety bound to the first oligonucleotide.

In another aspect of the invention, the quenching oligonucleotide possesses secondary and/or tertiary structure. That is, the oligonucleotide is presented in a folded conformation that effectively renders it more compact than a linear conformation. A variety of environmental conditions may then act on the oligonucleotide to remove such secondary or tertiary structure, such as the action of an enzyme or binding factor, the presence of an appropriate complementary nucleic acid, or an increase in temperature.

The oligonucleotides of the invention are covalently bound to at least one quenching moiety, but may be optionally substituted by additional quenching moieties, that may be the same or different. In one aspect, the oligonucleotide is bound to a single quenching moiety. The quenching moiety may be bound to the oligonucleotide at any location, but where the oligonucleotide is bound to a single quenching moiety, the quenching moiety is typically bound at or near the 3'- or 5'-terminus. Preferably, the quenching moiety is bound at the 5'-terminus for amplification assays, polymerization and elongation assays. For ligation assays, preferably the quenching moiety is bound at a 5'-terminus of one substrate while the second substrate has a free 5'-phosphate at its terminus, or the quenching moiety is bound at a 3'-terminus of one substrate while the second substrate has a free 3'-hydroxyl at its terminus. Where the quenching oligonucleotide is bound to a plurality of quenching moieties, they are typically incorporated throughout the oligonucleotide, but are typically not bound at either terminus.

In one embodiment, the oligonucleotide of the invention is covalently bound to a chemically reactive group, $R_x$ by a covalent linkage L. The reactive oligonucleotide is therefore useful for labeling a wide variety of organic or inorganic substances that contain or are modified to contain a complementary functional groups with suitable reactivity, resulting in chemical attachment of the oligonucleotide to the desired conjugated substance (Sc). The reactive group and finctional group are typically an electrophile and a nucleophile that can generate a covalent linkage. Alternatively, the reactive group is a photoactivatable group, and becomes chemically reactive only after illumination with light of an appropriate wavelength. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
| --- | --- | --- |
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| Aldehydes | amines/anilines | imines |
| aldehydes or ketones | hydrazines | hydrazones |
| aldehydes or ketones | hydroxylamines | oximes |
| alkyl halides | amines/anilines | akyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| Anhydrides | alcohols/phenols | esters |
| Anhydrides | amines/anilines | carboxamides |
| aryl halides | thiols | thiophenols |
| aryl halides | mines | ryl amines |
| Aziridines | thiols | thioethers |
| Boronates | glycols | boronate esters |
| carboxylic acids | amines/anilines | carboxamides |
| carboxylic acids | alcohols | esters |
| carboxylic acids | hydrazines | hydrazides |
| Carbodiimides | carboxylic acids | N-acylureas or anhydrides |
| Epoxides | thiols | thioethers |
| Haloacetamides | thiols | thioethers |
| Halotriazines | amines/anilines | aminotriazines |
| Halotriazines | alcohols/phenols | triazinyl ethers |
| imido esters | amines/anilines | amidines |
| Isocyanates | amines/anilines | ureas |
| Isocyanates | alcohols/phenols | urethanes |
| Isothiocyanates | amines/anilines | thioureas |
| Maleimides | thiols | thioethers |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. oxysuccinimidyl (—OC$_4$H$_4$O$_2$) oxysulfosuccinimidyl (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof; used to form activated aryl esters; or a carboxylic acid activated by a carbodiimide to form an anhydride or mixed anhydride OCOR$^a$ or OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 8-dimethylaminopropyl, or N-morpholinoethyl).
**Acyl azides can also rearrange to isocyanates The covalent linkage L binds the reactive group $R_x$ or conjugated substance $S_c$ to the oligonucleotide, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds and carbon-sulfur bonds. L typically includes ether, thioether, carboxamide, sulfonamide, urea, urethane or hydrazine moieties. Preferred L moieties have 1–20 nonhydrogen atoms selected from the group consisting of C, N, O and S; and are composed of any combination of ether, thioether, amine, ester, carboxamide, sulfonamide, hydrazide bonds and aromatic or heteroaromatic bonds. Preferably L is a combination of single carbon-carbon bonds and carboxamide or thioether bonds. The longest linear segment of the linkage L preferably contains 4–10 nonhydrogen atoms including one or two heteroatoms. Examples of L include substituted or unsubstituted polymethylene, arylene, alkylarylene or arylenealkyl. In one embodiment, L contains 1–6 carbon atoms; in another, L is a thioether linkage. In yet another embodiment, L has the formula —$(CH_2)_a(CONH(CH_2)_b)_z$—, where a is an integer from 0–5, b is an integer from 1–5 and z is 0 or 1.

The selection of covalent linkage to attach the oligonucleotide to the conjugated substance typically depends on the functional groups available on the substance to be conjugated. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of functional group may be available on the substance (typical for polysaccharides), or a variety of fimctional groups may occur (e.g. amines, thiols, alcohols, phenols), as is typical for proteins. Although some selectivity can be obtained by careful control of the reaction conditions, selectivity of labeling is best obtained by selection of an appropriate chemically reactive group $R_x$.

Typically, $R_x$ will react with an amine, a thiol or an alcohol. In one embodiment, $R_x$ is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a haloacetamide, a halotriazine, a hydrazine, an imido ester, an isocyanate, an isothiocyanate, a maleimide, a sulfonyl halide, or a thiol group. Preferably, $R_x$ is a carboxylic acid, a succinimidyl ester, an amine, a haloacetamide, an alkyl halide, a sulfonyl halide, an isothiocyanate, a maleimide group or an azidoperfluorobenzamido group.

In another embodiment of the invention, the quenching oligonucleotide and/or a second oligonucleotide hybridized to the quenching oligonucleotide is optionally covalently labeled with a fluorophore or fluorophores that do not have significant spectral overlap with that of the quenching moiety or with the associated nucleic acid stain. The emission of such a fluorophore is useful for quantitating the amount of the particular oligonucleotide in the reaction mixture.

In yet another embodiment of the invention, the quenching oligonucleotide and/or a second oligonucleotide hybridized to the quenching oligonucleotide, or their hybrid itself, contains a cleavage site for an enzyme or a binding site for a nucleic acid binding protein. Such oligonucleotides are useful for nuclease assays and for detecting the presence or activity of binding factors.

Quenching Moiety

Any synthetic dye that can detectably quench the luminescence of an associated nucleic acid stain is an acceptable quenching moiety for the purposes of the instant invention. Specifically, as used in the invention, the quenching moieties possess an absorption band that exhibits at least some spectral overlap with an emission band of the nucleic acid stain. This overlap may occur with emission of the donor occurring at a lower or even higher wavelength emission maximum than the maximal absorbance wavelength of the quenching moiety, provided that sufficient spectral overlap exists. Energy transfer may also occur through transfer of emission of the donor to higher electronic states of the acceptor. One of ordinary skill in the art determines the utility of a given quenching moiety by examination of that dye's excitation bands with respect to the emission spectrum of the nucleic acid stain to be used.

Typically, fluorescence quenching in the invention occurs through Fluorescence Resonance Energy Transfer (FRET) between a nucleic acid stain and a quenching moiety of the invention. The spectral properties of the donor and acceptor dyes have a strong effect on the degree of energy transfer observed, as does the separation distance between the nucleic acid stains associated with the oligonucleotide and the quenching moiety. As the separation distance increases, the degree of fluorescence quenching decreases. Whereas a stained quenching moiety-labeled 10-mer oligonucleotide may result in essentially no fluorescent signal, increasing the length of the labeled oligonucleotide results in less efficient quenching of the associated stains that are more distant from the quenching moiety. Oligonucleotides of substantial length (for example a 100-mer) will exhibit substantial fluorescence upon staining, due to the inability of the covalently bound quenching moiety to efficiently quench the fluorescence of more distant fluorescent stain molecules (FIG. 1).

The quenching moiety is attached to the oligonucleotide via a covalent linkage, L, as described above for attachment of the oligonucleotide to a reactive group or conjugated substance. Each L moiety is optionally the same or different.

In one embodiment, the quenching moiety is bound to the oligonucleotide at the 5'-terminus, a base, a sugar, or a phosphate via a covalent linkage that is a phosphate ester, a phosphoramidate linkage, a carboxamide linkage, a sulfonamide linkage, or a thioether linkage. Preferably, the quenching moiety is covalently bound to the oligonucleotide via one or more purine or pyrimidine bases wherein L is an amide, ester, ether or thioether bond, or transition metal complex; or is attached to a phosphate or a carbohydrate by a bond that is an ester, thioester, amide, ether, thioether, or transition metal complex.

In a preferred embodiment, the quenching moiety is bound to the oligonucleotide by a linkage L at the 5'-terminus. Alternatively, the quenching moiety is attached by formation of a noncovalent association of the nucleic acid with a photoreactive quenching moiety precursor, followed by illumination, resulting in covalent association.

In another preferred embodiment, the covalent linkage L between the quenching moiety and the oligonucleotide incorporates an amide bond, an ester bond, an ether bond, a thioether bond, or the covalent linkage L incorporates a platinum atom as described in U.S. Pat. No. 5,714,327 (incorporated by reference).

The quenching moiety is optionally fluorescent, provided that the maximal emission wavelength of the dye is well separated from the maximal emission wavelength of the nucleic acid stain when associated with nucleic acids. Preferably, however, the quenching moiety is only dimly fluorescent, or is essentially nonfluorescent, when covalently coupled to a nucleic acid or oligonucleotide.

Essentially nonfluorescent, as used herein, indicates that the fluorescence efficiency of the quenching moiety in an assay solution as described for any of the methods herein is less than or equal to 5 percent, preferably less than or equal to 1 percent. In another aspect of the invention, the covalently bound quenching moiety exhibits a quantum yield of less than about 0.1, more preferably less than about 0.01. In a preferred embodiment of the invention, the fluorescence of nucleic acid stains associated with a quenching oligonucleotide of the invention is quenched more than 50% relative to the same oligonucleotide associated with the same nucleic acid stain in the absence of the covalently bound quenching moiety. In another embodiment, the nucleic acid stains are quenched more than 90% relative to the unlabeled oligonucleotide. In yet another embodiment, the nucleic acid stains are quenched more than 95% relative to the unlabeled oligonucleotide.

A wide variety of chemically reactive dyes and fluorophores that are suitable for use as a quenching moiety are already known in the art (see for example MOLECULAR PROBES HANDBOOK, Sixth Ed., Richard P. Haugland, ed. (1996), in particular Chapters 1–3; MOLECULAR PROBES HANDBOOK, Seventh Ed., Richard P. Haugland, ed. (available on CD-ROM, 1999); BIOPROBES 26 (October 1997); BIOPROBES 27 (February 1998); BIOPROBES 28 (May 1998); BIOPROBES 29 (November 1998); BIOPROBES 30 (January 1999); BIOPROBES 31 (May 1999): BIOPROBES 32 (December 1999); and BIOPROBES 33 (February 2000); all incorporated by reference). The spectral properties of candidate dyes in solution or when conjugated to oligonucleotides are known or are readily measured using a spectrofluorometer.

Typically, the quenching moiety is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated and sulfonated derivatives thereof (as described in U.S. Pat. No. 5,830,912 to Gee et al. (1998) and U.S. Pat. No. 5,696,157 to Wang et al. (1997), incorporated by reference), a polyazaindacene (e.g. U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); 5,433,896 to Kang, et al.(1995); U.S. Pat. No. 6,005,113 to Wu et al. (1999), all incorporated by reference), a xanthene, an oxazine or a benzoxazine, a carbazine (U.S. Pat. No. 4,810,636 to Corey (1989), incorporated by reference), or a phenalenone or benzphenalenone (U.S. Pat. No. 4,812,409 Babb et al. (1989), incorporated by reference).

Other preferred quenching moieties that are essentially nonfluorescent dyes include in particular azo dyes (such as DABCYL or DABSYL dyes and their structural analogs), triarylmethane dyes such as malachite green or phenol red, 4',5z-diether substituted fluoresceins (U.S. Pat. No. 4,318, 846 (1982)), or asymmetric cyanine dye quenchers (PCT Int. App. WO 99 37,717 (1999)).

Where the quenching moiety is a xanthene, the synthetic dye is optionally a fluorescein, a rhodol (U.S. Pat. No. 5,227,487 to Haugland, et al. (1993), incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171 to Haugland, et al. (1990), incorporated by reference). Particularly preferred xanthenes include fluorinated derivatives of xanthene dyes (Int. Publ. No. WO 97/39064, Molecular Probes, Inc. (1997), incorporated by reference), and sulfonated derivatives of xanthene dyes (Int. Publ. No. WO 99/15517, Molecular Probes, Inc. (1999), incorporated by reference). As used herein, oxazines include resorufms, aminooxazinones, diaminooxazines, and their benzo-substituted analogs.

In a particularly preferred embodiment, the quenching moiety is an essentially nonfluorescent derivative of 3- and/or 6-amino xanthene that is substituted at one or more amino nitrogen atoms by an aromatic or heteroaromatic ring system (as described in provisional patent application Ser. No. 60/131,782, titled XANTHENE DYES AND THEIR APPLICATION AS LUMINESCENCE QUENCHING COMPOUNDS, by Haugland et al., filed Apr. 30, 1999, incorporated by reference). These quenching dyes typically have absorption maxima above 530 nm, have little or no observable fluorescence and efficiently quench a broad spectrum of luminescent emission, such as is emitted by chemilumiphores, phosphors, or fluorophores. In one embodiment, the quenching dye is a substituted rhodamine. In another embodiment, the quenching compound is a substituted rhodol.

The quenching moieties of the invention preferably have the formula

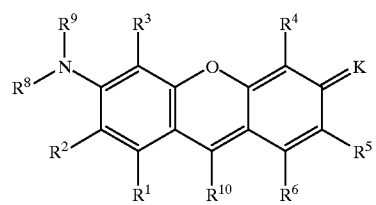

wherein K is O or $N^+R^{18}R^{19}$.

In a preferred embodiment of the invention, at least one of $R^8$, $R^9$, $R^{18}$ and $R^{19}$ is a Q ring system. Alternatively, either $R^8$ taken in combination with $R^9$, or $R^{18}$ taken in combination with $R^{19}$, forms a saturated 5- or 6-membered heterocycle that is a piperidine, or a pyrrolidine that is fused to a Q moiety. Typically one of $R^8$ and $R^9$ and one of $R^{18}$ and $R^{19}$ are each a Q, which are the same or different. In another embodiment, each of $R^8$, $R^9$, $R^{18}$ and $R^{19}$ is a Q, which may be the same or different.

The aromatic or heteroaromatic ring system, Q, has 1–4 fused aromatic or heteroaromatic rings, and is attached to the amino nitrogen by a single covalent bond. Where Q is fully aromatic and contains no heteroatom, Q comprises 1–4 fused six-membered aromatic rings. Where Q is heteroaromatic, Q incorporates at least one 5- or 6-membered aromatic heterocycle that contains at least 1 and as many as 4 heteroatoms that are selected from the group consisting of O, N, and S in any combination, that is optionally fused to an additional six-membered aromatic ring, or is fused to one 5- or 6-membered heteroaromatic ring that contains at least 1 and as many as 3 heteroatoms that are selected from the group consisting of O, N, and S in any combination.

Each Q is bound to the quenching moiety at a 3- or 6-amino nitrogen atom via a single covalent bond. In some embodiments, the amino nitrogen substituents, taken in combination, form a 5- or 6-membered heterocycle that is a piperidine, a morpholine, a pyrrolidine, a pyrazine, or a piperazine, and the Q ring system is fused to the resulting heterocycle adjacent to the xanthene nitrogen, so as to be formally bound to the amino nitrogen via single bond. Each Q may be bound to the amino nitrogen atom at either an aromatic or heteroaromatic ring, provided it is attached at a carbon atom of that ring.

Typically, each Q is independently a substituted or unsubstituted phenyl, naphthyl, anthracenyl, benzothiazole, benzoxazole, or benzimidazole. Where the amino nitrogen substituents form a 5- or 6-membered heterocycle and the Q ring system is fused to the resulting heterocycle, the heterocycle is typically a pyrrolidine ring and Q is typically a fused six-membered aromatic ring. Most preferably, Q is a phenyl or substituted phenyl.

Each Q is optionally and independently substituted by hydrogen, halogen, cyano, sulfo, alkali or ammonium salt of sulfo, carboxy, alkali or ammonium salt of carboxy, nitro, alkyl, perfluoroaLkyl, alkoxy, alkylthio, amino, monoalkylamino, dialkylamino or alkylamido, in any combination.

The remainder of $R^8$, $R^9$, $R^{18}$, and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxyhc acid, or a carboxylic acid ester of a $C_1$–$C_6$ alkyl. Alternatively, where $R^8$ in combination with $R^9$, or $R^{18}$ in combination with $R^{19}$, or both, forms a saturated 5- or 6-membered heterocyclic ring that is a piperidine, a morpholine, a pyrrolidine, a pyrazine, or a piperazine, that is optionally substituted by methyl, sulfonic acid, a salt of sulfonic acid, carboxylic acid, a salt of carboxylic acid, or a carboxylic acid ester of a $C_1$–$C_6$ alkyl. Alternatively, one or more of $R^8$ in combination with $R^2$, $R^9$ in combination with $R^3$, $R^{18}$ in combination with $R^4$, or $R^{19}$ in combination with $R^5$, forms a 5- or 6-membered ring that is saturated or unsaturated, and that is optionally substituted by one or more $C_1$–$C_6$ alkyls or —$CH_2SO_3X$, where X is H or a counterion.

$R^1$ and $R^6$ are H, or one or more of $R^1$ in combination with $R^2$, or $R^6$ in combination with $R^5$, is a fused six-membered aromatic ring.

Substituents $R^2$, $R^3$, $R^4$, and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$.

The pendant group $R^{10}$ is H, CN, a carboxylic acid, a salt of carboxylic acid, or a carboxylic acid ester of a $C_1$–$C_6$ alcohol. Alternatively $R^{10}$ is a saturated or unsaturated, branched or unbranched $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons. In another preferred embodiment, $R^{10}$ has the formula

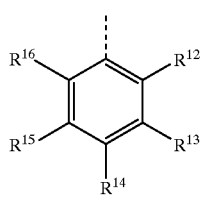

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino, azido; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_7$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons. Alternatively, a pair of adjacent substituents $R_{13}$ and $R^{14}$, $R^{14}$ and $R^{15}$, or $R_{15}$ and $R^{16}$, taken in combination, form a fused 6-membered aromatic ring that is optionally further substituted by carboxylic acid, or a salt of carboxylic acid.

As discussed above, the quenching moiety is covalently attached to the oligonucleotide of the invention by a covalent linkage, L. Typically, the covalent linkage is attached to the quenching moiety at one of $R^8$, $R^9$, $R^{12}$, $R^{13}$, $R^{14}$, $R_{15}$, $R^{16}$, $R^{18}$, or $R^{19}$ preferably at one of $R^{12}$–$R^{16}$, most preferably at $R^{12}$, $R^{14}$ or $R^{15}$, or as a substituent on a Q ring system. Alternatively, the covalent linkage incorporates an alkyl, alkoxy, alkylthio or alkylamino substituent. Typically, there is exactly one of $R^8$, $R^9$, $R^{12}$, $R^{13}$, $R^{14}$, $R^{15}$, $R^{16}$, $R^{18}$, or $R^{19}$ that is the covalent linkage to the oligonucleotide. Preferably, one of $R^{12}$, $R^{13}$, $R^{14}$, $R^{15}$, or $R^{16}$ is the covalent linkage to the oligonucleotide. Most preferably, one of $R^{12}$, $R^{14}$, and $R^{15}$ is the covalent linkage to the oligonucleotide.

In a preferred embodiment, the K moiety is $N^+R^{18}R^{19}$, such that the quenching moieties of the invention are rhodamines, and have the formula

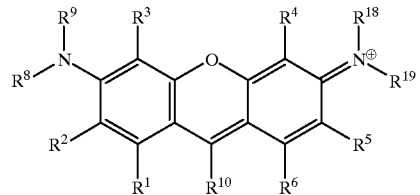

wherein at least one of $R^8$, $R^9$, $R^{18}$ and $R^{19}$ is a Q ring system. Preferably at least one of $R^8$ and $R^9$ is a Q and at least one of $R^{18}$ and $R^{19}$ is a Q, which may be the same or different.

In another embodiment, K is Q, such that the quenching moieties of the invention are rhodols, and have the formula

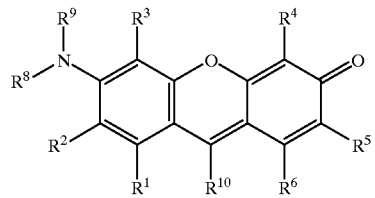

wherein at least one of $R^8$ and $R^9$ is a Q.

In another aspect of the invention, an oligonucleotide is covalently bound to a generally colorless precursor to a quenching moiety, that is chemically or enzymatically converted to a quenching dye. In this embodiment, the quenching moiety precursors have the formula

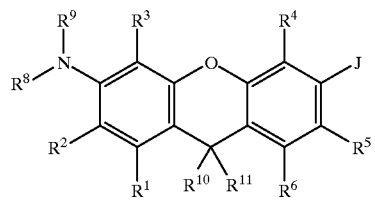

wherein J is O—$R^7$ or $NR^{18}R^{19}$, and $R^1$–$R^{19}$ is as defined above.

These precursors to the quenching dyes typically do not function as energy acceptors unless or until the aromaticity of the ring system is restored, as for the quenching moieties described above. In these precursors $R^7$ is H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl. Alternatively, $R^7$ is a monovalent radical formally derived by removing a hydroxy group from a carboxylic acid, a sulfonic acid, a phosphoric acid, or a mono- or polysaccharide, such as a glycoside. In another embodiment, $R^7$ is a photolabile caging group, such as described in Haugland, MOLECULAR PROBES HANDBOOK OF FLUORESCENT PROBES AND RESEARCH CHEMICALS, Sixth Ed., Chapter 19 (1996) (incorporated by reference).

$R^{10}$ is as defined previously, and $R^{11}$ is H, hydroxy, CN or alkoxy having 1–6 carbons. Alternatively, $R^{10}$ in combination with $R^{11}$ forms a 5- or 6-membered spirolactone ring, or $R^{11}$ in combination with $R^{12}$ forms a 5- or 6-membered spirolactone ring, or a 5- or 6-membered sultone ring.

These precursor compounds are readily converted to the fully conjugated quenching dyes of the invention by chemical, enzymatic, or photolytic means. These colorless precursors are typically conjugated to the oligonucleotide via the covalent linkage, L, as described above.

In another embodiment, the quenching moiety of the invention is a 3', 4'-dialkoxyfluorescein. Dialkoxyfluoresceins that are useful as quenching energy acceptors have been described previously (U.S. Pat. No. 4,318,846 to Khanna et al. (1982)). The dialkoxyfluoresceins useful as quenching moieties of the instant invention have the formula:

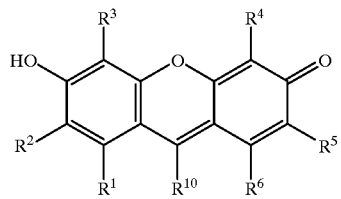

wherein $R^1$ and $R^6$ are H, or $R^1$ taken in combination with $R^2$, or $R^6$ taken in combination with $R^5$ is a fused six-membered aromatic ring. The substituents $R^2$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol. Alternatively, either or both of $R^2$ or $R^5$ is a sulfonate, —$SO_3X$ where X is H or a counterion. In another aspect of the invention, $R^2$ taken in combination with $R^1$ is a fused six-membered aromatic ring, or $R^5$ taken in combination with $R^6$ is a fused six-membered aromatic ring.

The $R^3$ and $R^4$ substituents are alkoxy groups having 1–6 carbons. The alkyl portions of the alkoxy groups are independently linear or branched, saturated or unsaturated.

The $R^{10}$ substituent is H, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino. Where any permitted $R^{10}$ substituent incorporates an alkyl portion, these alkyl groups independently have 1–6 carbons. Alternatively, $R^{10}$ has the formula

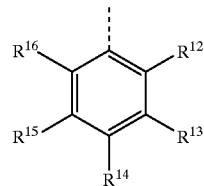

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of which have 1–6 carbons. Alternatively, one pair of adjacent substituents $R^{13}$ and $R^{14}$, $R^{14}$ and $R^{15}$ or $R^{15}$ and $R^{16}$, when taken in combination, form a fuised 6-membered aromatic ring that is optionally further substituted by carboxylic acid, or a salt of carboxylic acid. Typically one of $R^{12}$, $R^{13}$, $R^{14}$, $R^{15}$ and $R^{16}$ is the attachment point of the covalent linkage L, which is bound to the oligonucleotide.

In another embodiment, the quenching moiety is a triarylmethane dye having the formula:

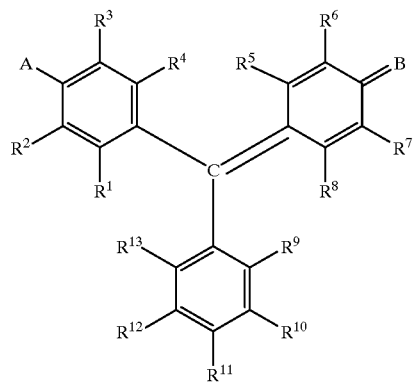

wherein the $R^1$, $R^2$, $R^3$, $R^4$, $R^5$, $R^6$, $R^7$, and $R^8$ substituents are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol. Any of $R^1$, $R^2$, $R^3$, $R^4$, $R^5$, $R^6$, $R^7$, and $R^8$ are optionally su —$SO_3X$ where X is H or a counterion. Alternatively, any adjacent substituents $R^1$ and $R^2$, $R^3$ and $R^4$, $R^5$ and $R^6$, or $R^7$ and $R^8$, when taken in combination, form a fused six-membered aromatic ring.

The A moiety is OH or $NR^{14}R^{15}$, where $R^{14}$ and $R^{15}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl. Alternatively one of $R^{14}$ and $R^{15}$ is a covalent linkage L. Alternatively, $R^{14}$ taken in combination with $R^{15}$ forms a saturated 5- or 6-membered heterocycle that is optionally fuirther substituted one or more times by methyl, carboxylic acid, a salt of carboxylic acid, a carboxylic acid ester of a $C_1$–$C_6$ aLkyl, or a covalent linkage L. In another aspect of the invention, $R^{14}$ in combination with $R^2$, or $R^{15}$ in combination with $R^3$, or both, form a 5- or 6-membered ring that is saturated or unsaturated, and is optionally substituted by one or more $C_1$–$C_6$ alkyls or —$CH_2SO_3X$.

The B moiety is O or $N^+R^{16}R^{17}$, where $R^{16}$ and $R^{17}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl. Alternativley, one of $R^{16}$ and $R^{17}$ is a covalent linkage L. Alternatively, $R^{16}$ taken in combination with $R^{17}$ forms a saturated 5- or 6-membered heterocycle that is optionally firther substituted one or more times by methyl, carboxylic acid, a salt of carboxylic acid, a carboxylic acid ester of a $C_1$–$C_6$ alkyl; or a covalent linkage L. In another aspect of the invention, $R^{16}$ in combination with $R^6$, or $R^{17}$ in combination with $R^7$, or both, form a 5- or 6-membered ring that is saturated or unsaturated, and is optionally substituted by one or more $C_1$–$C_6$ alkyls or —$CH_2SO_3X$.

The $R^9$, $R^{10}$, $R^{11}$, $R^{12}$ and $R^{13}$ substituents are independently H, F, Cl, Br, I, —$SO_3X$, a H carboxylic acid, a salt of carboxylic acid, CN, hydroxy, amino, hydrazino; or $C_1$–$C_{18}$ aLkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons.

In one aspect of the invention, $R^9$ is carboxylic acid, a salt of carboxylic acid, or —$SO_3X$. In another aspect of the invention, one pair of adjacent substituents $R^{10}$ and $R^{11}$, $R^{11}$ and $R^{12}$ or $R^{12}$ and $R^{13}$, when taken in combination, form a fused 6-membered aromatic ring that is optionally further substituted by carboxylic acid, or a salt of carboxylic acid. Typically, one of $R^9$, $R^{10}R^{11}$, $R^{12}$, $R^{13}$ and $R^{14}$ is a covalent linkage L that is in turn attached to the oligonucleotide.

Nucleic Acid Stains

Any luminophore with sufficient spectral overlap with a quenching moiety of the instant invention, as calculated above, is a suitable donor for the applications of the invention, provided that it exhibits sufficient affinity for at least some oligonucleotides and nucleic acids so that it will associate with them for a time sufficient that the luminescence measurements required by the instant methods may be taken. The instant nucleic acid stains are normally luminescent when associated noncovalently with nucleic acids, that is, they exhibit a detectable and useful luminescent signal when they are noncovalently associated with a nucleic acid that is not labeled with a quenching moiety as described herein. While fluorescent or fluorogenic stains are preferred for energy transfer applications, any nucleic acid stain that emits light (including chemiluminescence or phosphorescence) having sufficient spectral overlap with that of the quenching moieties on the oligonucleotide is also useful. In general, the greater the degree of spectral overlap (at any given separation distance), the greater the overall quenching observed.

While FRET is the most common mechanism for quenching to occur, any combination of molecular orientation and spectral coincidence that results in quenching of luminescence is a useful mechanism for quenching by the covalently bound quenching moiety, as described herein. For example, efficient quenching can occur even in the absence of spectral overlap if the luminophore and the quenching moiety are sufficiently close together to form a ground-state complex (as described in Tyagi et al., NATURE BIOTECHNOLOGY 16, 49 (1998)).

In one embodiment of the invention, the nucleic acid stain is a phenanthridinium dye, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example).

In a preferred embodiment of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR, SYTO, SYTOX, PICOGREEN, OLIGREEN, and RIBOGREEN from Molecular Probes, Inc., Eugene, Oreg.

In another preferred embodiment of the invention, the nucleic acid stain is a monomeric, homodimeric or heterodimeric cyanine dye that incorporates an aza- or polyaza-benzazolium heterocycle, such as an azabenzoxazole, azabenzimidazole, or azabenzothiazole, that gives an enhanced fluorescence when associated with nucleic acids. Any of the dyes described in provisional application Ser. No. 60/131,782, titled AZA-BENZAZOLIUM CONTAINING CYANINE DYES, by Haugland et al., filed Apr. 3, 1999 (application incorporated by reference) may be used, including nucleic acid stains commercially available under the trademarks SYTO, SYTOX, JOJO, JO-PRO, LOLO, LO-PRO from Molecular Probes, Inc., Eugene, Oreg.

The nucleic acid stain is selected to have the desired relative nucleic acid binding affinity and spectral characteristics, according to methods well known in the art.

Matching the spectral properties of a given nucleic acid stain to the spectral properties of a given quenching moiety requires comparing the absorption and emission spectra of each dye to insure that sufficient spectral overlap occurs for efficient energy transfer. The spectral properties of selected nucleic acid stains when bound to nucleic acids are provided in Table 2.

TABLE 2

| Nucleic Acid Stain | Ex/Em (nm/nm)* |
|---|---|
| 4',6-(Diimidazolin-2-yl)-2-phenylindole | 364/455 |
| 4',6-Diamidino-2-phenylindole | 358/461 |
| 7-Aminoactinomycin D | 546/647 |
| 9-Amino-6-chloro-2-methoxyacridine | 419/483 |
| Acridine homodimer | 431/498 |
| Acridine orange | 500/526 (DNA) |
|  | 460/650 (RNA) |
| BOBO-1 | 462/481 |
| BOBO-3 | 570/604 |
| BO-PRO-1 | 462/481 |
| BO-PRO-3 | 575/599 |
| Dihydroethidium | 518/605 |
| Ethidium bromide | 518/605 |
| Ethidium diazide | 432/496 (unbound) |
| Ethidium homodimer-1 | 528/617 |
| Ethidium homodimer-2 | 535/624 |
| Ethidium monoazide | 464/625 (unbound) |
| Ethidium-acridine heterodimer | 455 and 532/619 |
| Hexidium iodide | 518/600 |
| Hoechst 33258 (bis-benzimide) | 352/461 |
| Hoechst 33342 | 350/461 |
| Hydroxystilbamidine, methanesulfonate | 385/emission varies |
| JOJO-1 | 529/545 |
| JO-PRO-1 | 530/546 |
| LDS 751 | 543/712 |
|  | 590/607 (RNA) |
| LOLO-1 | 565/579 |
| LO-PRO-1 | 567/580 |
| OLIGREEN ssDNA quantitation reagent | 498/518 (random sequence 40-mer) |
| PICOGREEN dsDNA quantitation reagent | 502/523 |
| POPO-1 | 434/456 |
| POPO-3 | 534/570 |
| PO-PRO-1 | 435/455 |
| PO-PRO-3 | 539/567 |
| Propidium iodide | 535/617 |
| SYBR Green I nucleic acid gel stain | 494/521 |
| SYBR Green II RNA gel stain | 492/513 |
| SYTO 11 green fluorescent nucleic acid stain | 508/527 |
| SYTO 12 green fluorescent nucleic acid stain | 499/522 |
| SYTO 13 green fluorescent nucleic acid stain | 488/509 |
| SYTO 14 green fluorescent nucleic acid stain | 517/549 |
| SYTO 15 green fluorescent nucleic acid stain | 516/546 |
| SYTO 16 green fluorescent nucleic acid stain | 488/518 |
| SYTO 17 red fluorescent nucleic acid stain | 621/634 |
| SYTO 17 red fluorescent nucleic acid stain | 621/634 |
| SYTO 20 green fluorescent nucleic acid stain | 512/530 |
| SYTO 21 green fluorescent nucleic acid stain | 494/517 |
| SYTO 22 green fluorescent nucleic acid stain | 515/535 |
| SYTO 23 green fluorescent nucleic acid stain | 499/520 |
| SYTO 24 green fluorescent nucleic acid stain | 490/515 |
| SYTO 25 green fluorescent nucleic acid stain | 521/556 |
| SYTO 40 blue fluorescent nucleic acid stain | 420/441 |
| SYTO 41 blue fluorescent nucleic acid stain | 430/454 |
| SYTO 42 blue fluorescent nucleic acid stain | 433/460 |
| SYTO 43 blue fluorescent nucleic acid stain | 436/467 |
| SYTO 44 blue fluorescent nucleic acid stain | 446/471 |
| SYTO 45 blue fluorescent nucleic acid stain | 455/484 |
| SYTO 59 red fluorescent nucleic acid stain | 630/645 |
| SYTO 60 red fluorescent nucleic acid stain | 652/678 |
| SYTO 61 red fluorescent nucleic acid stain | 628/645 |
| SYTO 62 red fluorescent nucleic acid stain | 652/676 |
| SYTO 63 red fluorescent nucleic acid stain | 657/673 |
| SYTO 64 red fluorescent nucleic acid stain | 599/619 |
| SYTO 80 orange fluorescent nucleic acid stain | 531/545 |
| SYTO 81 orange fluorescent nucleic acid stain | 530/544 |
| SYTO 82 orange fluorescent nucleic acid stain | 541/560 |
| SYTO 83 orange fluorescent nucleic acid stain | 543/559 |
| SYTO 84 orange fluorescent nucleic acid stain | 567/582 |
| SYTO 85 orange fluorescent nucleic acid stain | 567/583 |
| SYTOX Blue nucleic acid stain | 445/470 |
| SYTOX Green nucleic acid stain | 504/523 |
| SYTOX Orange nucleic acid stain | 547/570 |

TABLE 2-continued

| Nucleic Acid Stain | Ex/Em (nm/nm)* |
|---|---|
| Thiazole Orange | 509/525 |
| TO-PRO-1 | 515/531 |
| TO-PRO-3 | 642/661 |
| TO-PRO-5 | 747/770 |
| TOTO-1 | 514/533 |
| TOTO-3 | 642/660 |
| YO-PRO-1 | 491/509 |
| YO-PRO-3 | 612/631 |
| YOYO-1 | 491/509 |
| YOYO-3 | 612/631 |

*All excitation and emission maxima were determined for dyes bound to double-stranded calf thymus DNA in aqueous solution, unless otherwise indicated.
†After the dihydroethidium is oxidized.

Aplications

The combination of quenching oligonucleotides and luminescent nucleic acid stains are useful in any application where it is desirable to minimize the fluorescent signal from selected oligonucleotides used in the application.

Typically, the selected oligonucleotides are prepared by attachment of the appropriate quenching moiety (as described above). The labeled oligonucleotides are then combined with a reaction mixture that contains a plurality of nucleic acid stain molecules, such that the nucleic acid stain molecules associate non-covalently with the oligonucleotide. The associated nucleic acid stain molecules then undergo energy transfer to said quenching moiety, such that the fluorescence of the nucleic acid stain molecules is detectably decreased.

In one aspect of the invention, the quenching oligonucleotides are used in conjunction with a reaction mixture for performing the polymerase chain reaction (PCR), real-time PCR, the strand displacement assay (SDA), the ligase chain reaction (LCR), nucleic acid sequence-based amplification (NASBA), Q beta replicase-based amplification, cycling probe reaction (CPR), solid phase amplification (SPA) or self sustained sequence replication (3SR) to decrease background fluorescence upon staining the amplified product mixture with a fluorescent nucleic acid stain.

FIG. 3 depicts the components present at the beginning of a typical PCR amplification reaction of a target strand of nucleic acid (starting materials), and the amplification products in the first, second and subsequent rounds of amplification.

Figure 4:
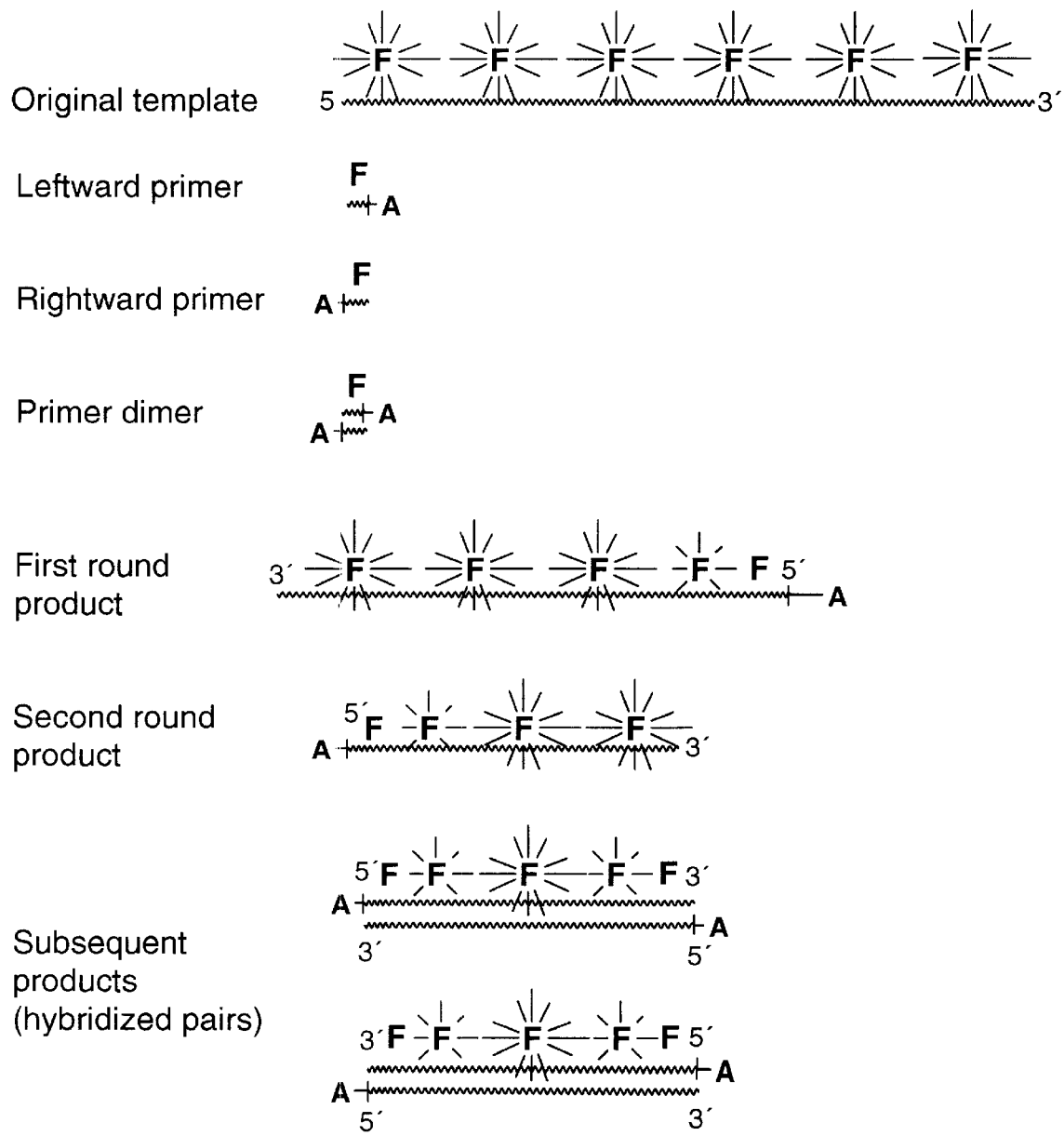
FIG. 4: Fluorescent staining of PCR amplification products where the primers used are covalently labeled with a quenching moiety.

FIG. 4. depicts the results of staining the products of a PCR amplification where the primers used are covalently labeled with a quenching moiety. The labeled primers present in the mixture are essentially completely quenched, as are any primer dimers formed. While the original nucleic acid template is not quenched, the template is typically present as a relatively minor component when compared to the number of copies of the target sequence that are produced, as are the products of first-round amplification. The target sequence is only slightly quenched by the presence of the quenching moiety, and is readily quantified by selection of an appropriately sensitive fluorescent nucleic acid stain.

By utilizing the oligonucleotides of the invention as the primers in the PCR amplification, background fluorescence from residual primers or dimers of residual primers is essentially eliminated, resulting in substantially more accurate determination of the amount of amplified product sequence present in the amplification mixture.

In another aspect of the invention, the combination of quenching oligonucleotides and fluorescent nucleic acid stains is used to assay for the presence or activity of a selected protein. This method typically requires preparing a mixture comprising a quenching oligonucleotide and a nucleic acid stain such that said nucleic acid stain associates noncovalently with the oligonucleotide with concomitant quenching of the luminescence of the nucleic acid stain. To this mixture is added a sample that contains or is thought to contain a protein of interest. After incubation of the mixture it is illuminated and the resulting luminescence is correlated with the presence or activity of the protein of interest, typically by comparison with a calibration curve, or with luminescence values obtained for positive or negative controls.

In one embodiment, the protein is an enzyme, such as a ligase or nuclease. Where the quenching oligonucleotide is exposed to a nuclease enzyme (e.g. DNAse or RNase) in the presence of a fluorescent nucleic acid stain, initial cleavage of the oligonucleotide by a nonspecific endonuclease results in oligonucleotide fragments that are no longer in proximity to the quenching moiety, but that still bind nucleic acid stain to become fluorescent. Fluorescence initially increases but, with additional exposure to the nuclease, the fluorescent signal decreases, providing an indication of the presence of the nuclease enzyme, the enzyme activity, and the rate of enzymatic cleavage.

Certain nucleases, such as restriction endonucleases, recognize specific sequences in double- or single-stranded nucleic acids, or have a strong preference for cleaving at sites containing only purines or only pyrimidines. Where the quenching oligonucleotide comprises a cleavage site for a site-specific nuclease, then cleavage at that site releases a nucleic acid fragment that is no longer in proximity to the quenching moiety but that still binds a nucleic acid stain to become fluorescent. The fluorescence of the fragment containing the quenching moiety is not fluorescent, and the intact template is not fluorescent. Measuring the resulting increase in fluorescence after treatment with the enzyme provides an accurate measure of the relative activity, presence and abundance of the nuclease.

Selected enzymes, such as exonucleases, cleave single nucleotides from either the 3'- or 5'-terminus of the oligonucleotide. Where the quenched oligonucleotide of the invention is sufficiently long, the nucleic acid stains that are associated with the oligonucleotide at sufficient distance from the quenching moiety will exhibit substantial fluorescence. As nucleotides are cleaved from the terminus distant from the quenching moiety, overall fluorescence will decrease, until the shortened oligonucleotide becomes essentially nonfluorescent, thus providing a measure of the activity or abundance of the enzyme.

Certain proteins and complexes recognize specific sequences in single- or double-stranded nucleic acids. If such a sequence is incorporated into a quenching oligonucleotide, then binding of the cognate factor disrupts transfer of energy from the donor nucleic acid stain to the quenching moiety. This disruption is achieved by changing the flexibility or rigidity of the nucleic acid, thus affecting the interaction between the dyes, or by affecting the secondary structure of the nucleic acid, thus affecting the angle of the resulting dipoles of the donor and quencher dyes with respect to one another. Since some nucleic acid binding proteins (binding factors) bend DNA significantly upon binding, the resulting bound nucleic acid stains are quenched less upon binding. Other environmental factors also affect the secondary and/or tertiary structure of the quenching oligonucleotide, such as the presence of specific enzymes, a complementary strand of nucleic acid, or an increase in temperature. As loss of secondary or tertiary structure typically places associated nucleic acid stain molecules at a greater distance from the quenching moiety, overall luminescence quenching is reduced. In this way, the environmental factor of choice may be detected or quantitated.

In another aspect, the invention comprises the use of quenched oligonucleotide primers to reduce background fluorescence when the primers are used for template-directed strand elongation by DNA or RNA polymerases or reverse transcriptases and elongation products are detected using nucleic acid stains. In such assays, the quenched oligonucleotide primer is elongated by addition of nucleotides (usually to the 3' terminus of the primer) by the appropriate enzyme, usually in a template-directed manner. Enzymes such as terminal deoxynucleotidyl transferase add nucleotides to a primer in a non-template directed manner, but can be assayed in the same way. The nucleic acid stain that associates with the primer is essentially non-fluorescent or exhibits strongly diminished fluorescence, but when the oligonucleotide is extended sufficiently, associated nucleic acid stains are no longer efficiently quenched and the oligonucleotide becomes more strongly fluorescent. The rate at which fluorescence arises and the amount of resulting fluorescence are measures of the activity or abundance of the enzyme in the sample.

In yet another aspect, the invention comprises the use of quenched single- or double-stranded oligonucleotides to reduce the background fluorescence in assays for DNA or RNA ligases, splicing enzymes, or telomerases when the products of such reactions are detected using nucleic acid stains. In these assays, the enzyme of interest catalyzes the formation of a covalent bond between the two termini of single- or double-stranded nucleic acids. Some enzymes, such as T4 DNA ligase, form covalent linkages between double-stranded DNA fragments. Other enzymes, such as T4 RNA ligase, form covalent linkages between single-stranded DNA or RNA fragments. In these assays, there are two single- or double-stranded oligonucleotides used as substrates. One oligonucleotide of the invention is labeled at one terminus and the other oligonucleotide is not labeled. Nucleic acid stains associated with the unlabeled oligonucleotide are fuilly fluorescent, while nucleic acid stains associated with the quenching moiety-labeled oligonucleotide are essentially nonfluorescent or exhibit strongly diminished fluorescence. When the enzyme joins the two oligonucleotides, the resulting ligation product exhibits decreased fluorescence when stained, relative to the non-ligated oligonucleotides. The resulting decrease in fluorescence or the rate of decrease is a measure of the activity or abundance of the enzyme in the sample.

In another aspect, the invention comprises the use of quenched single-stranded oligonucleotides in hybridization assays, in which the products of hybridization are detected using nucleic acid stains. Single-stranded oligonucleotides bind nucleic acid stains of the invention and form fluorescent complexes. When those single-stranded oligonucleotide complexes hybridize to probes that have an acceptor coupled to them, the fluorescence of the associated nucleic acid stains is quenched relative to those associated with the original complex. Thus hybridization can be monitored as a decrease in fluorescence. This fluorescence decrease can be used as a measure of the abundance of the target nucleic acid in the original sample, of the presence or absence of a target nucleic acid, or of the sequence of the target nucleic acid, if hybridization conditions are chosen appropriately. For example, a single mismatch or single base polymorphism or mutation can be identified as the lack of fluorescence decrease upon exposure of the sample to hybridization conditions, due to lack of resulting formation of the hybrid. Even large single-stranded target sequences can be identified in this way, as long as the observed decrease in fluorescence is large enough to ensure that the measurement is accurate, relative to the background of unhybridized fluorescent target nucleic acid.

The examples below are given so as to illustrate the practice of this invention. They are not intended to limit or define the entire scope of this invention.

EXAMPLE 1

Preparation of aryl-substituted rhodamine compounds

Aryl and heteroaryl substituted xanthylium dyes are readily prepared by displacement of the chloro groups from a 3,6-dichlorofluoran or a 3,6-dichlorosulfofluoran using the desired substituted amine (U.S Pat. No. 4,258,118 and German Patent 24 60 491).

Where the amine used is N-methylaniline, the resulting quenching moiety has the following formula:

Compound 1

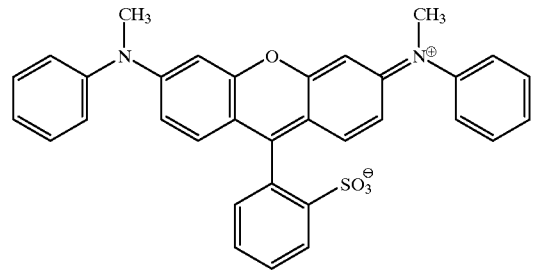

Where the amine used is indoline (2,3-dihydroindole), the resulting quenching moiety has the following formula:

Compound 2

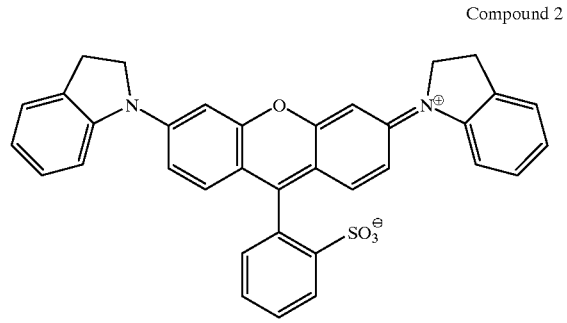

Where the amine used is aniline, the resulting quenching moiety has the following formula:

Compound 3

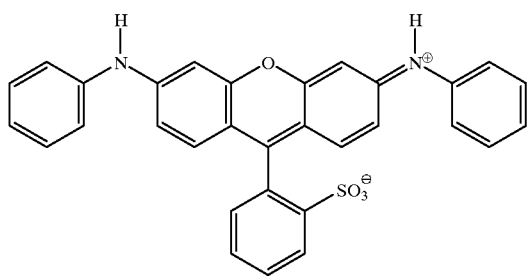

EXAMPLE 2

Preparation of chemically reactive quenching moieties (Compound 6)

Compound 1 of Example 1 (2 g) is heated in 20 mL of phosphorous oxychloride at 70° C. for 6 hours. The solution is evaporated under reduced pressure and the residue is dried in vacuo for several hours to yield the sulfonyl chloride derivative (Compound 4).

Compound 4

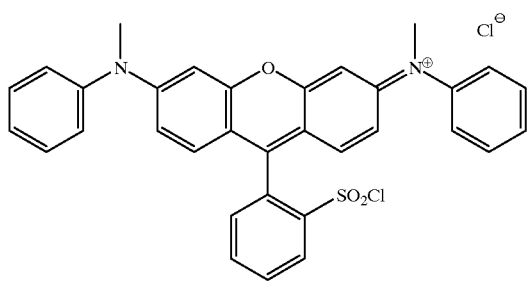

Isonipecotic acid (20.5 g) is heated at reflux for 30 minutes in 80 mL of hexamethyldisilazane in the presence of a catalytic amount of concentrated sulfuric acid. Excess hexamethyldisilazane is evaporated and the residue is dissolved in 150 mL of acetonitrile and cooled to 0–5° C. Triethylamine (23 mL) is added, followed by 29 g of Compound 2 in 150 mL of acetonitrile to generate Compound 3, which is isolated by evaporation of the solvent, addition of 1 M HCl, extraction into chloroform and evaporation.

Compound 5

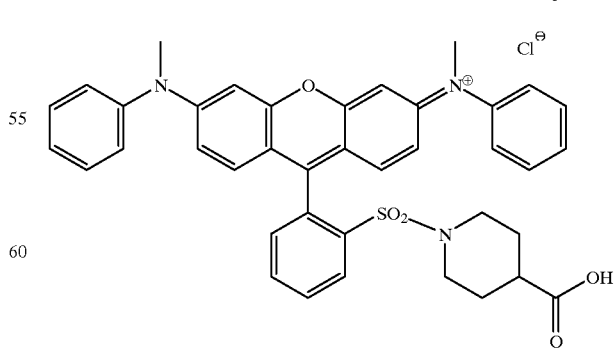

To a stirring solution of Compound 5 (2.26 g) in 20 mL of acetonitrile at room temperature are added sequentially 1.1 mL of diisopropylethylamine and 1.7 g of 2-succinimido-1,1,3,3-tetramethyluronium tetrafluoroborate. The resulting mixture is stirred at room temperature for one hour. The solution is partitioned between CHCl$_3$ and 1 M HCl, and the organic portion is evaporated and recrystallized from CH$_3$CN and diethyl ether to yield the desired succinimidyl ester, Compound 6.

Compound 6

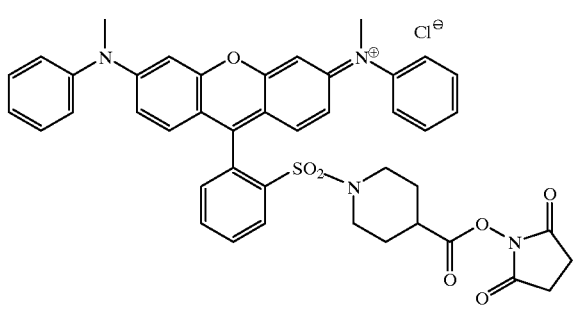

EXAMPLE 3

Prelaration of a reactive 6uenchin moiety
(Compound 8)

To Compound 4 (Example 2, 1.5 g) in 20 mL of methylene chloride is added 0.72 mL of chlorosulfonic acid, followed by 4.5 mL of acetic anhydride. The mixture is stirred at room temperature overnight and 100 mL of ether is added precipitate the crude product. Purification is by chromatography on a silica gel column eluting with 9:1 acetonitrile/wateer to yield 1.0 g of the pure sulfonated derivative Compound 7.

Compound 7

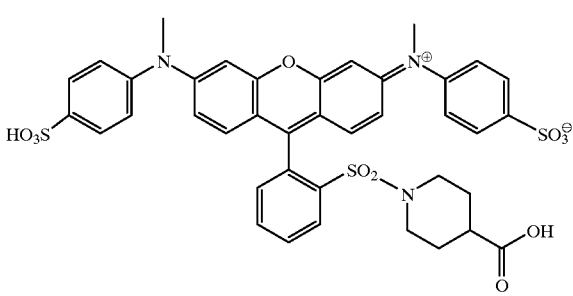

To 0.6 g of Compound 7 in 60 mL of DMF at room temperature is added 0.48 mL of diisopropylethylamine and 0.93 g of 2-succinimido-1,1,3,3-tetramethyluronium tetrafluoroborate. The mixture is stirred for 30 minutes. Ethyl acetate (240 mL) is added. The mixture is stirred overnight and the product Compound 8 is recovered by filtration.

Compound 8

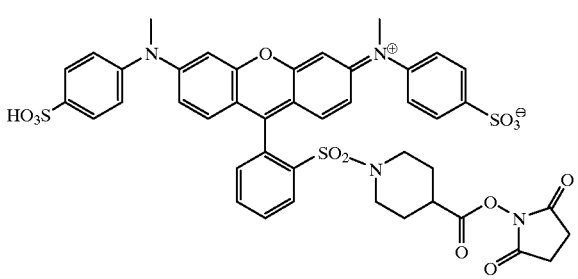

EXAMPLE 4

Prearation of a reactive guenching moiety
(Compound 11)

A mixture of 2 g of Compound 2 (Example 1) and 20 mL of phosphorous oxychloride is heated at 65° C. for 6 hours. Excess reagents are removed under vacuum and the residue is dissolved in 50 mL of acetonitrile and cooled to ca. 10° C. To this solution is added 9.2 mL of diisopropylethylamine and 10.8 mL of ethyl isonipecotate. After 2 hours the acetonitrile is removed under vacuum and the reaction is worked up with 1 M HCl and extracted into chloroform. The crude product is purified on a silica gel column to yield 1.88 g of the pure ester Compound 9.

Compound 9

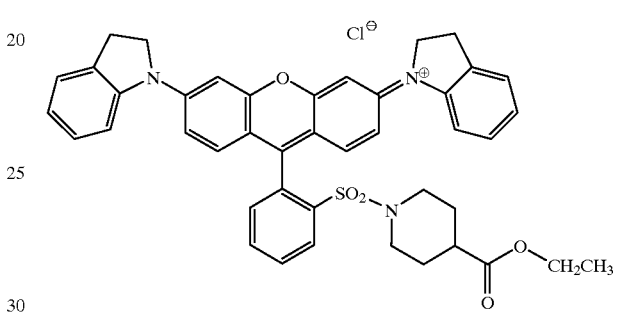

To 0.31 g of Compound 9 in 60 mL of methanol is added 1.5 mL of a 10% NaOH solution and the mixture is heated at 35–40° C. overnight. Another 2 mL of 10% NaOH is introduced and heating is continued for another 20 hours. The reaction mixture is cooled to room temperature, 120 mL of 1 M HCl is added and after another hour the product is filtered to give Compound 10.

Compound 10

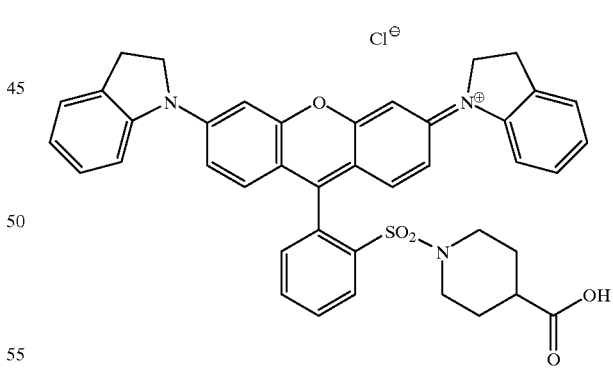

To 98 mg of Compound 10 in 1.5 mL of DMF is added 0.07 mL of diisopropylethylamine and 66 mg of 2-succinimido-1,1,3,3-tetramethyluronium tetrafluoroborate. The reaction is worked up with chloroform and 1 M HCl and the organic extracts are dried over magnesium sulfate. The crude material is dissolved in 2 mL of acetonitrile. Ethyl acetate (8 mL) is added dropwise and after stiring overnight the solution is filtered to yield 80 mg of Compound 11.

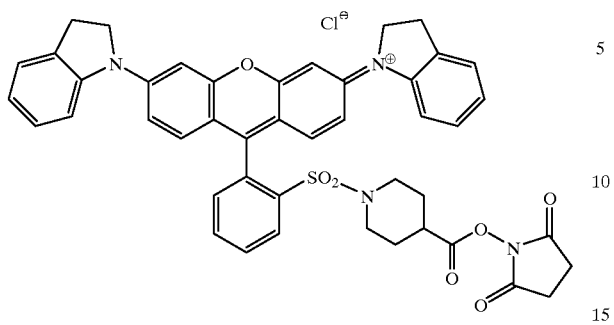

Compound 11

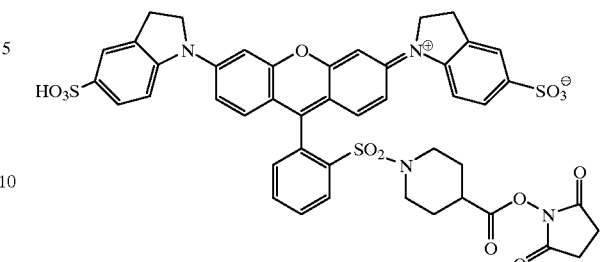

Compound 14

EXAMPLE 5

Preparation of a reactive quenching moiety (Compound 14)

To 0.2 g of Compound 9 in 5 mL of methylene chloride is added 1 mL of acetic anhydride and 71 μL of chlorosulfonic acid. After stirring overnight at room temperature, ethyl acetate (15 mL) is added dropwise and Compound 12 is recovered by filtration.

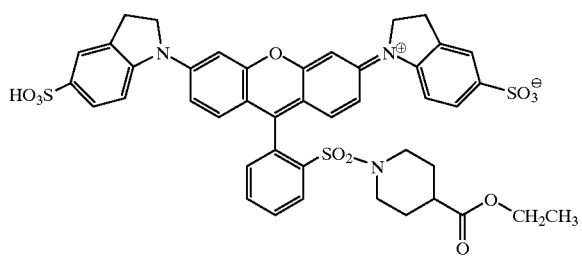

Compound 12

Compound 12 (100 mg) is hydrolyzed by stirring in 25 mL of methanol and 2 mL of 10% NaOH at 35° C. overnight. HCl (10 mL of 1 M) is added, the volume is reduced to 5 mL and then filtered to yield Compound 13.

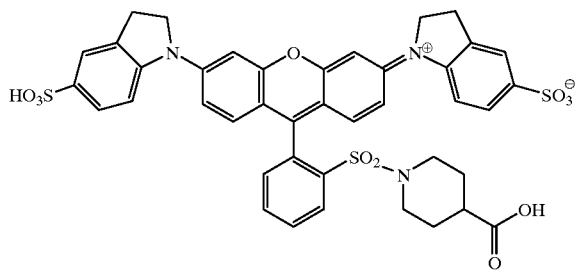

Compound 13

Diisopropylethylamine (34 μL) and 30 mg of 2-succinimido-1,1,3,3-tetramethyluronium tetrafluoroborate are added to 44 mg of Compound 13 in 2 mL of DMF. After 15 minutes at room temperature, ethyl acetate (4 mL) is added and the mixture is filtered to yield the crude product. This is stirred in 5 mL of acetonitrile for 30 minutes and filtered again to yield Compound 14.

EXAMPLE 6

Preparation of a reactive guenchinm moiety (Compound 16)

Compound 3 of Example 1 (0.375 g) is heated with 5 mL' of phosphorous oxychloride at 60–65° C. for 4 hours. Excess reagent is removed under reduced pressure and to the crude sulfonyl chloride is added 40 mL of acetonitrile, followed by addition of a mixture of 2.3 g of ethyl isonipecotate and 2.42 mL of triethylamine in 10 mL of acetonitrile. After stirring at room temperature for one hour, volatiles are removed by evaporation under reduced pressure. To the residue is added 60 mL of methanol followed by 20 mL of 10% NaOH. The mixture is heated at 50° C. for one hour. The volume is reduced to about ⅓ and 90 mL of 2 M HCl is added at 0° C. The solid is collected by filtration and dried in vacuo to yield 0.43 g of the crude nipecotic acid derivative Compound 15.

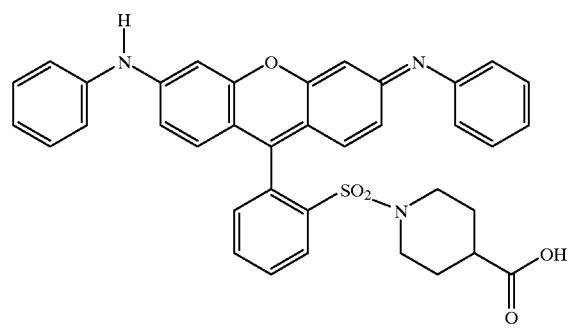

Compound 15

To 100 mg of acid Compound 15 in 6 mL of DMF and 0.2 mL of pyridine is added 192 mg of 1-[3-(dimethylamino)propyl]-3-ethylcarbodiimide hydrochloride and 115 mg of N-hydroxysuccinimide. After stirring overnight at room temperature, the DMF solution is added to 100 mL of cold 1 M HCl and filtered to yield Compound 16.

Compound 16

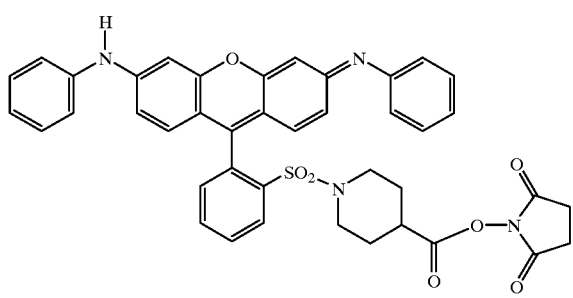

EXAMPLE 7

Prearation of a reactive quenching moiety
(Compound 19)

A mixture of 5.52 g of 3-hydroxydiphenylamine, 2.21 g of phthalic anhydride, and 2.04 g of ZnCl$_2$ is heated at 180° C. for 1.5 hour. A mixture of methanol (150 mL) and water (50 mL) is added and the mixture is heated at reflux overnight. The solid is filtered and then refluxed again in 100 mL of methanol and 50 mL of water for 3 hours. The mixture is filtered to yield Compound 17.

Compound 17

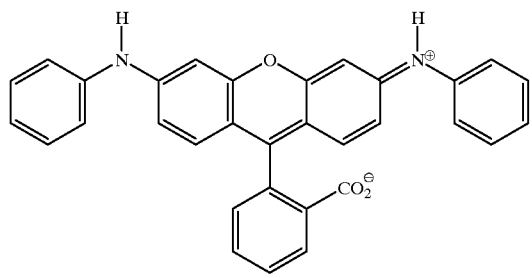

Compound 17 (1.5 g) is heated at 70–75° C. in 15 mL of phosphorous oxychloride overnight to generate the acid chloride. Volatiles are removed under reduced pressure. The residue is dissolved in 30 mL of DMF followed by the addition of 2.4 mL of triethylamine and 2.37 g of ethyl isonipecotate. After several hours at room temperature, the DMF is removed and the residue is dissolved in 30 mL of chloroform and chromatographed on silica gel to yield 0.65 g of the ethyl ester Compound 18.

Compound 18

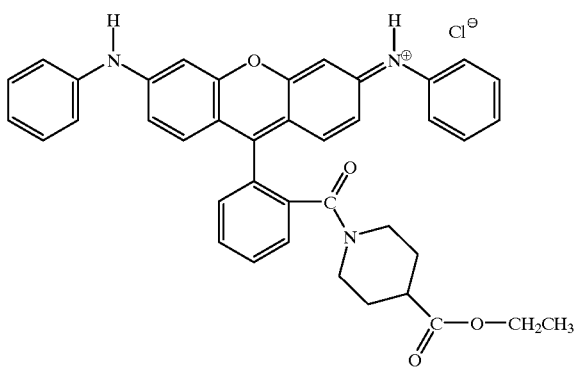

Compound 18 is hydrolyzed by stirring in 15 mL of methanol and 2 mL of 10% NaOH at 35° C. for 2 hours. HCl (60 mL of 1 M) is added dropwise and the mixture is filtered to yield 0.61 g of the crude acid. 65 mg of this acid is converted to its succinimidyl ester by stirring with 0.147 g of 1-[3-(dimethylamino)propyl]-3-ethylcarbodiimide hydrochloride, 89 mg of N-hydroxysuccinimide, and 0.2 mL of pyridine in 2 mL of DMF at room temperature for 20 hours. The mixture is then added to 50 mL of cold 1 M HCl and filtered to yield 58 mg of Compound 19.

Compound 19

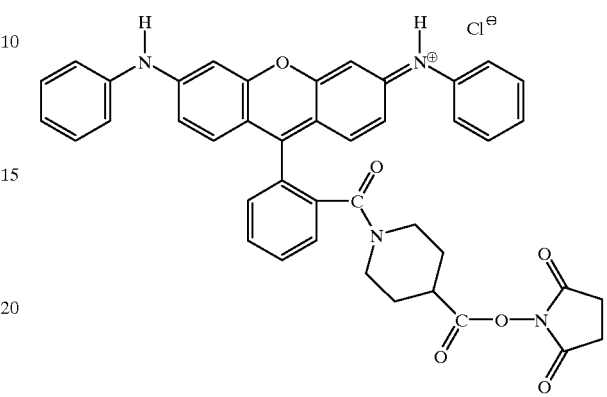

EXAMPLE 8

Quenching the fluorescence of nucleic acid stains bound to oligonucleotides in solution.

Eighteen-base oligonucleotide conjugates of quencher dyes are prepared using standard methods. Essentially, a primary amine is synthetically incorporated on the 5' end of the oligonucleotide as a phosphoramidite and reacted subsequently with a succinimidyl ester quencher dye. Alternatively, conjugates are prepared by reacting a quencher maleimide with a thiol that has been incorporated via a phosphoramidite. Conjugates are purified by reverse phase HPLC. Solutions containing 200 ng/mL of each of the conjugates are prepared in 10 mM Tris, pH 7.8, 1 mM EDTA, containing 0.5 μm nucleic acid stain and the fluorescence of the mixture is measured. As a control, the fluorescence of the nucleic acid stain bound to an equal concentration of unconjugated oligonucleotide of the same sequenc,e is measured. The degree of quenching is defined as the fluorescence of 0.5 μM of the nuclcic acid stain-bound conjugate minus the fluorescence of the same concentration of the nucleic acid stain alone. All dyes are able to quench the fluorescence of the nucleic acid stains, provided that the emission of the donor dye shows some overlap with the absorption of the quencher dye. Some quenchers are able to efficiently quench the fluorescence of a wide variety of nucleic acid stains (Table 3). In some cases the quenched sample has lower fluorescence than the unbound dye. All of the quenchers are at least as efficient as DABCYL and many are much mote efficient, particularly for quenching dyes with emission wavelengths greater than 500 nm. Quenchers with long wavelength absorption maxima are especially superior for quenching nucleic acid stains with long wavelength emissions.

EXAMPLE 9

Quenching nucleic acid stains bound to oligonucleotides in gels or in capillary electrophoresis Ohgonucleotide primers labeled with quencher dyes, prepared as described above (Example 8), are separated by electrophoresis in polyacrylamide or agarose gels, or are separated in capillary electrophoresis, or using microfluidic methods, along with unlabeled primers and PCR products or other products of primer extension. The gels are then stained with an appropriate nucleic acid gel stain, such as ethidium bromide, SYBR Green I stain, SYBR Green II stain, a red fluorescent SYTO stain, SYBR Gold stain, SYTO blue stain, SYTO green stain, or SYTO orange stain. Alternatively, the capillary electrophoresis is performed min the presence of the stain, using standard methods. Primers labeled with the quencher dyes are essentially nonfluorescent in the presence of the fluorescent nucleic acid stain, and thus do not contribute appreciably to the staining pattern in the gel. This simplified pattern facilitates automated gel or capillary electrophoresis analysis. Similarly quenched primers or ligation monomers can be eliminated from the staining pattern in a ligation assay containing one labeled and one unlabeled oligonucleotide, or a telomerase assay. Primer dimers with quenchers on both 5' ends are also not detected by fluorescence because their fluorescence is essentially fully quenched, so that even if they are abundant they do not obscure signals due to short amplification products.

EXAMPLE 10

Quenching olgonucleotide primers in PCR reactions

PCR reactions are prepared, using oligonucleotide primers labeled with quencher Compound 16 or 19. SYBR Green I stain is included at a dilution of 1:50,000 of the commercially available stock solution, or PICOGREEN reagent is added to the reaction after PCR is completed at a final concentration of 0.8 $\mu$M, and the fluorescence of the solution is measured. If SYBR Green I stain is included in the reaction, then the reaction can be monitored in real time, using an appropriate instrument, such as the LIGHTCYCLER (Roche) or the GENEAMP 9700 (Perkin Elmer). The background fluorescence in reactions containing quenched primers is lower than that observed in those containing unlabeled primers, and in addition, primer dimers do not contribute to the product signal. Other stains, such as YOYO-1 or OLIGREEN reagent, are added to the solution after PCR with the same results. Other stains, such as YO-PRO-1, are added to the solution prior to or during PCR with essentially the same results.

EXAMPLE 11

Labeling large DNA molecules with platinum quencher dye complexes

A quencher platinum complex is synthesized, (using the methods essentially as described in U.S. Pat. No. 5,714,327, incorporated by reference) and a 1 mg/mL solution of the quencher complex is prepared in water. This solution is then diluted into water, and 10 ng to 3 $\mu$g of the quencher complex is added to a microfuge tube containing 500 ng of plasmid DNA. The volume is brought to 25 $\mu$L with water, and the samples heated at 65° C. for 15 minutes. Five $\mu$L of 1% diethyldithiocarbamic acid, sodium salt, solution is added to stop the reaction, samples are mixed and cooled to room temperature, and 10 $\mu$L of each reaction is loaded onto a 1% agarose minigel. The gel is electrophoresed in 0.5× TBE buffer (45 mM Tris-borate, 1 mM EDTA, pH 8), stained with SYBR Gold stain, and photographed with 300 nm transillumination, through a SYBR Gold photographic filter. Samples labeled with 10 ng to 0.3 $\mu$g of the quencher complex are very fluorescent. Samples labeled with 0.5 $\mu$g to 1 $\mu$g of the quencher complex show only weak fluorescence. Samples labeled with 1.5 $\mu$g to 3 $\mu$g of the quencher complex are essentially nonfluorescent. Similarly, samples labeled with sufficient amounts of the quencher complex are able to quench the fluorescence of bound hybridization probes that are themselves covalently labeled with reactive fluorophore labels or fluorescent nucleotides.

TABLE 3

Fluorescence quenching by selected quenched oligonucleotides when associated with selected nucleic acid stains.
Relative Fluorescence[1]

| Nucleic acid stain | Ex/Em[2] (nm) | Free dye[3] | Quenching Moiety | | | | | | |
|---|---|---|---|---|---|---|---|---|---|
| | | | DABCYL | Cpd. 6 | Cpd. 8 | Cpd. 11 | Cpd. 14 | Cpd. 16 | Cpd. 19 |
| POPO-1 | 434/456 | 2.6 | 8.7 | 10 | 6.1 | 3.5 | 6.1 | | |
| PO-PRO-1 | 435/455 | 9.9 | 23 | 21 | 25 | 21 | 22 | | |
| SYTO 43 | 438/460 | 35 | 39 | 35 | 43 | 41 | 44 | | |
| BOBO-1 | 462/481 | 16 | 30 | 40 | 33 | 41 | 27 | | |
| SYBR Green I | 494/521 | 3.7 | 7.9 | 4.9 | 5.1 | 4.0 | 6.0 | 2.7 | 28 |
| PicoGreen reagent | 493/525 | 3.2 | 9.4 | 5.3 | 4.2 | 3.6 | 6.8 | 4.0 | 29 |
| OliGreen reagent | 498/515 | 4.3 | 9.6 | 7.1 | 5.2 | 4.3 | 6.4 | 4.2 | 27 |
| SYBR Gold stain | 494/530 | 3.2 | 7.7 | 4.0 | 4.0 | 4.0 | 5.3 | | |
| YO-PRO-1 | 491/509 | 4.3 | 16 | 9.9 | 8.8 | 6.5 | 8.9 | 6.0 | 34 |
| YOYO-1 | 491/509 | 13 | 24 | 23 | 11 | 12 | 9.2 | 8.9 | 9.2 |
| Ethidium bromide | 518/605 | 95 | 99 | 87 | 97 | 86 | 89 | 75 | 83 |
| JOJO-1 | 529/545 | 1.7 | 2.8 | 1.4 | | | | | |
| BOBO-3 | 570/604 | 76 | 60 | 56 | 64 | 60 | 64 | | |
| YOYO-3 | 612/631 | 6.9 | 38 | 28 | 8.9 | 5.2 | 5.1 | | |
| SYTO 59 | 630/645 | 9.1 | 61 | 27 | 15 | 6.3 | 11 | | |
| SYTO 61 | 630/645 | 12 | 60 | 37 | 23 | 6.9 | 12 | | |

[1]Relative fluorescence is the percentage of fluorescence exhibited by an quenching moiety-labeled oligonucleotide stained with the indicated nucleic acid stain relative to that of an unlabeled oligonucleotide of the same sequence, stained with the same amount of nucleic acid stain.
[2]Ex/em designates the fluorescence excitation and emission maxima for the indicated nucleic acid stain, bound to double-stranded DNA.
[3]Free dye indicates the relative fluorescence exhibited by the nucleic acid stain alone, expressed as a percentage of the fluorescence of the unlabeled oligonucleotide of the same sequence, bound to the same amount of nucleic acid stain. In some cases, the binding of particular quencher conjugates reduced the fluorescence of the nucleic acid stain solution to a level lower than that observed for free, unbound stain.

What is claimed is:

1. A method for decreasing detectable luminescence of nucleic acid stain molecules that are noncovalently associated with an oligonucleotide, said method comprising:

a) preparing the oligonucleotide by covalently attaching a quenching moiety to the oligonucleotide, wherein said quenching moiety is essentially nonfluorescent;

b) combining said oligonucleotide with a plurality of nucleic acid stain molecules such that the nucleic acid stain molecules associate noncovalently with said oligonucleotide;

wherein said nucleic acid stain molecules normally exhibit a luminescence when associated noncovalently with nucleic acids, and said nucleic acid stain molecules undergo energy transfer to said quenching moiety, such that said luminescence is detectably decreased.

2. A method, as claimed in claim 1, wherein said nucleic acid stain is a phenanthridinium dye, an acridine dye, an indole dye, an imidazole dye, a cyanine dye, or a homo- or heterodimer thereof.

3. A method, as claimed in claim 1, wherein said nucleic acid stain is an unsymmetrical cyanine dye or a dimer of an unsymmetrical cyanine dye.

4. A method, as claimed in claim 1, wherein said oligonucleotide has 6–60 bases.

5. A method, as claimed in claim 1, wherein the oligonucleotide is a primer useful for the amplification of a nucleic acid.

6. A method, as claimed in claim 5, wherein the amplification of the nucleic acid results from a polymerase chain reaction.

7. A method, as claimed in claim 1, wherein the oligonucleotide possesses secondary structure, tertiary structure, or both secondary and tertiary structure.

8. A method, as claimed in claim 1, wherein said covalently bound quenching moiety is a xanthene dye, a phenoxazine dye, a triarylmethane dye, or an azo dye.

9. A method, as claimed in claim 8, wherein said covalently bound quenching moiety is an N-aryl rhodamine dye, an N-heteroaryl rhodamine dye, an N-aryl rhodol dye, an N-aryl phenoxazine dye, a 4',5'-dialkoxyluorescein dye, a triarylmethane dye, or an azo dye.

10. A method, as claimed in claim 1, wherein said covalently bound quenching moiety is an N,N'-diaryl rhodamine dye.

11. A method of amplifying a target nucleic acid sequence, comprising:

a) preparing a reaction mixture comprising one or more polymerase enzymes, the target nucleic acid sequence, and a quenching primer;

wherein said quenching primer is an oligonucleotide having 6–60 nucleotides that is covalently bound to a quenching moiety;

b) incubating said reaction mixture under conditions such that the target nucleic acid sequence is amplified to produce an amplification product mixture;

c) adding a nucleic acid stain before, during, or after said incubating step, such that the nucleic acid stain associates noncovalently with the nucleic acids present in said amplification product mixture;

wherein said nucleic acid stain normally exhibits a luminescence when associated noncovalently with nucleic acids, and the luminescence of said nucleic acid stain that is associated with said quenching primer or a dimer of said quenching primer is detectably quenched; and d) illuminating said amplification product mixture to yield a luminescence response.

12. A method, as claimed in claim 11, further comprising quantitating said resulting amplification products.

13. A method, as claimed in claim 11, wherein said amplification product mixture is electrophoretically separated.

14. A method, as claimed in claim 11, wherein said polymerase enzyme is a DNA polymerase, an RNA polymerase, a reverse transcriptase, or a combination thereof.

15. A method, as claimed in claim 11, wherein said luminescence response of said amplification product mixture is used to determine the presence or activity of the amplification enzyme.

16. A method, as claimed in claim 11, wherein said luminescence response of said amplification product mixture is used to determine the rate or extent of amplification.

17. A method, as claimed in claim 11, wherein the covalently bound quenching moiety is a xanthene, a coumarin, naphthalene, an anthracene, a pyrene, a stilbene, a carbostyryl, a pyridine, a quinoline, an acridine, a cyanine, a polyazaindacene, an oxazine, a styryl, or an azo dye.

18. A method, as claimed in claim 11, wherein said covalently bound quenching moiety is a xanthene dye, a phenoxazine dye, a triarylmethane dye, or an azo dye.

19. A method, as claimed in claim 11, wherein said covalently bound quenching moiety is an N,N'-diaryl rhodamine dye or a 4',5'-dialkoxyfluorescein dye.

20. A method of elongating an oligonucleotide comprising:

a) preparing a mixture comprising an elongation enzyme and a quenching primer; wherein said quenching primer is an oligonucleotide having 6–60 nucleotides that is covalently bound to a quenching moiety;

b) incubating said mixture under conditions such that the quenching primer is extended to produce an elongation product;

c) adding a nucleic acid stain before, during, or after said incubating step, such that the nucleic acid stain associates noncovalently with the nucleic acids present in said mixture;

wherein said nucleic acid stain normally exhibits a luminescence when associated noncovalently with nucleic acids, and said luminescence due to nucleic acid stain associated with said primer or a dimer of said primer is detectably quenched; and d) illuminating said mixture to yield a luminescence response.

21. A method, as claimed in claim 20, further comprising quantitating said resulting elongation products.

22. A method, as claimed in claim 20, wherein said elongation enzyme is a terminal transferase.

23. A method, as claimed in claim 20, wherein said elongation enzyme is a telometase.

24. A method, as claimed in claim 20 wherein said luminescence response of said mixture is used to determine the presence or activity of the elongation enzyme.

25. A method, as claimed in claim 20, wherein said luminescence response of said mixture is used to determine the extent or rate of elongation.

26. A method, as claimed in claim 20, wherein said quenching moiety is a xanthene dye, a triarylmethane dye, or an azo dye.

27. A method, as claimed in claim 20, wherein said quenching moiety is an N-aryl rhodamine dye, an N-heteroaryl rhodamine dye, an N-aryl rhodol dye, and N-aryl phenoxazine dye, or an azo dye.

28. A method of assaying for a protein, comprising:
 a) preparing a mixture comprising
  i) a quenching oligonucleotide, wherein said quenching oligonucleotide is an oligonucleotide having 6–60 nucleotides that is covalently bound to a quenching moiety; and
  ii) a nucleic acid stain, wherein said nucleic acid stain normally exhibits a luminescence when associated noncovalently with nucleic acids;
   such that said nucleic acid stain associates noncovalently with the oligonucleotide, and the luminescence due to the nucleic acid stain associated with said oligonucleotide is detectably quenched;
 c) adding a sample that contains or is thought to contain said protein to said mixture;
 d) incubating the mixture for a time sufficient for said protein to interact with said oligonucleotide;
 e) illuminating said mixture to yield a luminescence response; and
 f) correlating said luminescence response with the presence or activity of said protein.

29. A method, as claimed in claim 28, wherein said protein is an enzyme.

30. A method, as claimed in claim 29, wherein said enzyme is a nuclease enzyme or a ligase enzyme.

31. A method, as claimed in claim 28, wherein said protein is a nucleic acid binding factor.

32. A composition, comprising
 an oligonucleotide having 6–60 bases;
 a quenching moiety that is covalently bound to said oligonucleotide, wherein said quenching moiety is essentially nonfluorescent; and
 a plurality of nucleic acid stain molecules, which may be the same or different, that are associated non-covalently with said oligonucleotide; wherein said nucleic acid stain molecules normally exhibit a luminescence when associated noncovalently with nucleic acids;
  wherein at least one of said nucleic acid stain molecules undergoes energy transfer of said luminescence to said quenching moiety.

33. A composition, as claimed in claim 32, wherein the quenching moiety has a maximum absorbance at about 450 to about 650 nm.

34. A composition, as claimed in claim 32, wherein the quenching moiety is a xanthene dye, a triarylmethane dye, or an azo dye.

35. A composition, as claimed in claim 34, wherein the covalently bound quenching moiety is a 4',5'-dialkoxyfluorescein or a triarylmethane dye.

36. A composition, as claimed in claim 35, wherein said quenching moiety has the formula

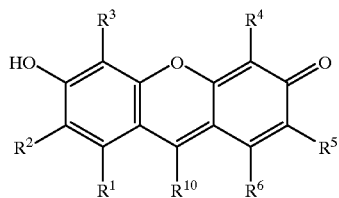

wherein
 $R^1$ is H, or $R^1$ taken in combination with $R^2$ is a fuised six-membered aromatic ring;
 $R^2$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$ where X is H or a counterion; or $R^2$ taken in combination with $R^1$ is a fused six-membered aromatic ring; or $R^5$ taken in combination with $R^6$ is a fused six-membered aromatic ring;
 $R^3$ and $R^4$ are independently $C_1$–$C_6$ alkoxy, the alkyl portions of which are linear or branched, saturated or unsaturated;
 $R^6$ is H, or $R^6$ taken in combination with $R^5$ is a fused six-membered aromatic ring;
 $R^{10}$ is H, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one or more times by F, Cl, Br, carboxylic acid, a salt of carboxylic acid, a carboxylic acid ester of a $C_1$–$C_6$ alcohol, —$SO_3X$, amino, alkylamino, or dialkylamino, the alkyl groups of which have 1–6 carbons; or $R^{10}$ has the formula

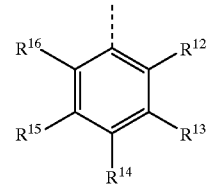

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R_{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; or one of $R^{12}$, $R^{13}$, $R^{14}$, $R^{15}$ and $R^{16}$ is a covalent linkage L;
 provided that at least one of $R^{10}$, $R^{12}$, $R^{13}$, $R^{14}$, $R^{15}$, $R^{16}$, $R^{18}$, or $R^{19}$ is a covalent linkage to said oligonucleotide, L, wherein L is a single covalent bond, or a linear or branched, cyclic or heterocyclic, saturated or unsaturated covalent linkage having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds.

37. A composition, as claimed in claim 35, wherein the covalently bound quenching moiety is a triarylmethane dye having the formula

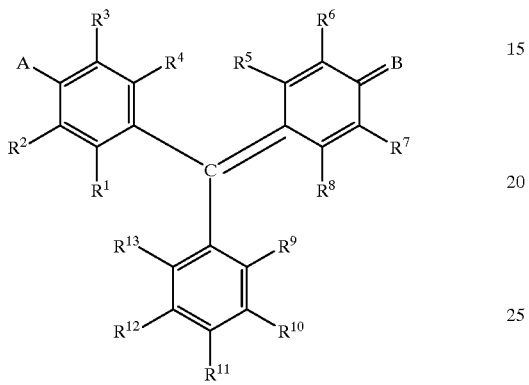

wherein $R^1$, $R^2$, $R^3$, $R^4$, $R^5$, $R^6$, $R^7$, and $R^8$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$ where X is H or a counterion; or $R^1$ and $R^2$, $R^3$ and $R^4$, $R^5$ and $R^6$, or $R^7$ and $R^8$, taken in combination form a fused six-membered aromatic ring;

A is OH or $NR^{14}R^{15}$;

wherein $R^{14}$ and $R^{15}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or a covalent linkage L; or $R^{14}$ taken in combination with $R^{15}$ forms a saturated 5- or 6-membered heterocycle that is optionally further substituted by methyl, carboxylic acid, a salt of carboxylic acid, a carboxylic acid ester of a $C_1$–$C_6$ alkyl, or a covalent linkage L; or $R^{14}$ in combination with $R^2$, or $R^{15}$ in combination with $R^3$, or both, form a 5- or 6-membered ring that is saturated or unsaturated, and is optionally substituted by one or more $C_1$–$C_6$ alkyls or —$CH_2SO_3X$;

B is O or $N^+R^{16}R^{17}$;

wherein $R^{16}$ and $R^{17}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or a covalent linkage L; or $R^{16}$ taken in combination with $R^{17}$ forms a saturated 5- or 6-membered heterocycle that is optionally further substituted by methyl, carboxylic acid, a salt of carboxylic acid, a carboxylic acid ester of a $C_1$–$C_6$ alkyl; or a covalent linkage L; or $R^{16}$ in combination with $R^6$, or $R^{17}$ in combination with $R^7$, or both, form a 5- or 6-membered ring that is saturated or unsaturated, and is optionally substituted by one or more $C_1$–$C_6$ alkyls or —$CH_2SO_3X$;

where $R^9$, $R^{10}$, $R^{11}$, $R^{12}$ and $R^{13}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{10}$ and $R^{11}$, $R^{11}$ and $R^{12}$ or $R^{12}$ and $R^{13}$, when taken in combination, form a fuised 6-membered aromatic ring that is optionally further substituted by carboxylic acid, or a salt of carboxylic acid; or one of $R^9$, $R^{10}R^{11}$, $R^{12}$, $R^{13}$ and $R^{14}$ is a covalent linkage L;

provided that at least one of $R^{14}$, $R^{15}$, $R^{16}$, $R^{17}$, $R^9$, $R^{10}$, $R^{11}$, $R^{12}$, $R_{13}$, $R^{14}$, or $R^{15}$ is a covalent linkage to said oligonucleotide, L, wherein L is a single covalent bond, or a linear or branched, cyclic or heterocyclic, saturated or unsaturated covalent linkage having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds.

38. A composition, as claimed in claim 34, wherein the covalently bound quenching moiety has the formula

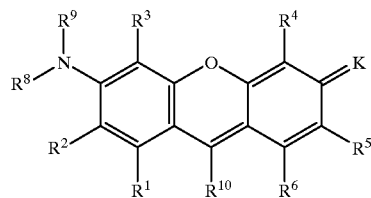

wherein $R^1$ is H, or $R^1$ taken in combination with $R^2$ is a fused six-membered aromatic ring;

$R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$ where X is H or a counterion; or $R^2$ taken in combination with $R^1$ is a fused six-membered aromatic ring; or $R^5$ taken in combination with $R^6$ is a fused six-membered aromatic ring;

$R^6$ is H, or $R^6$ taken in combination with $R^5$ is a fused six-membered aromatic ring;

$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or a covalent linkage L; or one or more of $R^8$ and $R^9$ is a Q moiety; or $R^8$ taken in combination with $R^9$ forms a saturated 5- or 6-membered heterocycle that is optionally fused to a Q moiety and optionally further substituted by methyl, carboxylic acid, a salt of carboxylic acid, a carboxylic acid ester of a $C_1$–$C_6$ alkyl, or a covalent linkage L; or $R^8$ in combination with $R^2$, or $R^9$ in combination with $R^3$, or both, form a 5- or 6-membered ring that is saturated or unsaturated, and is optionally substituted by one or more $C_1$–$C_6$ alkyls or —$CH_2SO_3X$;

wherein each Q moiety is 1–4 fused aromatic or heteroaromatic rings that is optionally substituted by halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino; alkylamidol; or a covalent linkage L; wherein each heteroaromatic ring in Q is a 5- or 6-membered aromatic heterocycle having 1 to 3 heteroatoms selected from the group consisting of O, N or S in any combination; and K is O or $N^+R^{18}R^{19}$;

wherein $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a w carboxylic acid ester of a $C_1$–$C_6$ alkyl; or a covalent linkage L; or one or more of $R^{18}$ and $R^{19}$ is a Q moiety; or $R^{18}$ taken in combination with $R^{19}$ forms a saturated 5- or 6-membered heterocycle that is a piperidine, or a pyrrolidine that is optionally fused to a Q moiety, and optionally further substituted by methyl, carboxylic acid, a salt of carboxylic acid, a carboxylic acid ester of a $C_1$–$C_6$ alkyl; or a covalent linkage L;

or $R^{18}$ in combination with $R^4$, or $R^{19}$ in combination with $R^5$, or both, form a 5- or 6-membered ring that is saturated or unsaturated, and is optionally substituted by one or more $C_1$–$C_6$ alkyls or —$CH_2SO_3X$ moieties;

$R^{10}$ is H, CN, a carboxylic acid, a salt of carboxylic acid, or a carboxylic acid ester of a $C_1$–$C_6$ alcohol; or $R^{10}$ is a saturated or unsaturated $C_1$–$C_{18}$ alkyl that is optionally substituted one more times by F, Cl, Br, carboxylic acid, a salt of carboxylic acid, a carboxylic acid ester a $C_1$–$C_6$ alcohol, —$SO_3X$, amino, alkylamino, or dialkylamino, the alkyl groups of which have 1–6 carbons; or $R^{10}$ has the formula

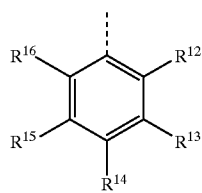

where $R^{12}$, $R^{13}$, $R^{14}$, $R^{15}$ and $R^{16}$ are independently H, F, Cl, Br, I, —$SO_3X$; a carboxylic acid, a salt of carboxylic acid, CN, hydroxy, amino, hydrazino; or $C_1$–$C_{18}$ alkyl, $C_1$–$C_{18}$ alkoxy, $C_1$–$C_{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; or one of $R^{12}$, $R^{13}$, $R^{14}$, $R^{15}$ and $R^{16}$ is a covalent linkage L;

provided that at least one of $R^8$, $R^9$, $R^{18}$, and $R^{19}$ is, or is fused to, a Q moiety; and further provided that at least one of $R^8$, $R^9$, $R^{12}$, $R^{13}$, $R^{14}$, $R^{15}$, $R^{16}$, $R^{18}$, or $R^{19}$ is a covalent linkage to said oligonucleotide, L, wherein L is a single covalent bond, or a linear or branched, cyclic or heterocyclic, saturated or unsaturated covalent linkage having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds.

39. A composition, as claimed in claim 38, wherein for said covalently bound quenching moiety:

each Q moiety is a substituted or unsubstituted phenyl, naphthyl, anthracenyl, benzothiazole, benzoxazole, or benzimidazole;

K is $N^+R^{18}R^{19}$;

$R^8=R^{19}$ and $R^9=R^{18}$; and $R^{10}$ has the formula

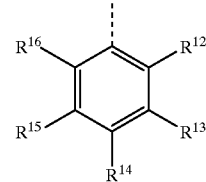

wherein one of $R^{12}$–$R^{16}$ is the covalent linkage L.

40. A composition, as claimed in claim 39, wherein each Q moiety is a phenyl or substituted phenyl; and $R^{12}$ is the covalent linkage L; wherein L is bound to the oligonucleotide at the 5'-terminus, a base, a sugar, or a phosphate.

41. A composition, as claimed in claim 40, wherein the covalent linkage L is bound to the oligonucleotide at one or more purine or pyrimidine bases through an amide, ester, ether or thioether bond, or a transition metal complex.

42. A composition, as claimed in claim 40, wherein the covalent linkage L is bound to the oligonucleotide at the 5'-terminus.

43. A composition, as claimed in claim 32, further comprising a second oligonucleotide that is hybridized to said oligonucleotide.

44. A composition, as claimed in claim 32, wherein the nucleic acid stain is a monomeric cyanine dye, a dimeric cyanine dye, a phenanthridinium dye, an acridine dye, an indole dye, or a Hoechst dye.

45. A composition, as claimed in claim 42, wherein the nucleic acid stain is Hoechst 33258, Hoechst 33342, Hoechst 34580, ethidium, ethidium dimer, propidium, aminoactinomycin, DAPI, or acridine orange.

46. A composition, as claimed in claim 42, wherein the nucleic acid stain is an unsymmetrical cyanine dye or a dimer of an unsymmetrical cyanine dye.

47. A composition, as claimed in claim 44, wherein the nucleic acid stain exhibits a maximum absorption at from about 350 nm to about 520 nm when associated noncovalently with a nucleic acid.

48. A composition, as claimed in claim 32, further comprising additional nucleotides covalently attached at the 3'-terminus of said oligonucleotide.

49. A composition, as claimed in claim 32, wherein said oligonucleotide is covalently bound to one or more additional quenching moieties, that may be the same or different.

50. A kit, comprising:
a) a nucleic acid stain that normally exhibits a luminescence when associated noncovalently with nucleic acids; and
b) an oligonucleotide having 6–60 bases that is covalently bound to a quenching moiety capable of accepting energy transfer of said luminescence from said nucleic acid stain, wherein said quenching moiety is essentially nonfluorescent.

51. A kit, as claimed in claim 50, wherein said quenching moiety is a xanthene dye, a phenoxazine dye, a triarylmethane dye, or an azo dye.

52. A kit, as claimed in claim 51, wherein said quenching moiety is an N-aryl rhodamine dye, an N-heteroaryl rhodamine dye, an N-aryl rhodol dye, an N-aryl phenoxazine dye, a 4',5'-dialkoxyfluorescein dye, a triarylmethane dye, or an azo dye.

53. A kit, as claimed in claim 50, wherein said quenching moiety has the formula

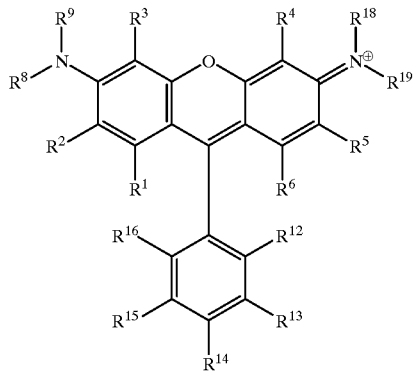

wherein
$R^1$ is H, or $R^1$ taken in combination with $R^2$ is a fused six-membered aromatic ring;
$R^2$, $R^3$, $R^4$ and $R^5$ are independently H, F, Cl, Br, I, CN; or $C_1$–$C_{18}$ alkyl, or $C_1$–$C_{18}$ alkoxy, where each alkyl or alkoxy is optionally further substituted by F, Cl, Br, I, a carboxylic acid, a salt of carboxylic acid, or a carboxylic acid ester of a $C_1$–$C_6$ alcohol; or —$SO_3X$ where X is H or a counterion; or $R^2$ taken in combination with $R^1$ is a fused six-membered aromatic ring; or $R^5$ taken in combination with $R^6$ is a fused six-membered aromatic ring;
$R^6$ is H, or $R^6$ taken in combination with $R^5$ is a fused six-membered aromatic ring;
$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoaLkyl, wherein the alkyl portions are optionally substituted by amino, hydroxy, carboxylic acid, a salt of carboxylic acid, or a carboxylic acid ester of a $C_1$–$C_6$ alkyl; or a covalent linkage L; or one or more of $R^8$ and $R^9$ is a Q moiety; or $R^8$ taken in combination with $R^9$ forms a saturated 5- or 6-membered heterocycle that is optionally fused to a Q moiety and optionally further substituted by methyl, carboxylic acid, a salt of carboxylic acid, a carboxylic acid ester of a $C_1$–$C_6$ alkyl, or a covalent linkage L; or $R^8$ in combination with $R^2$, or $R^9$ in combination with $R^3$, or both, form a 5- or 6-membered ring that is saturated or unsaturated, and is optionally substituted by one or more $C_1$–$C_6$ alkyls or —$CH_2SO_3X$;

wherein each Q moiety is a substituted or unsubstituted phenyl, naphthyl, anthracenyl, benzothiazole, benzoxazole, or benzimidazole that is optionally substituted by halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino; alkylamido; or a covalent linkage L; wherein each heteroaromatic ring in Q is a 5- or 6-membered aromatic heterocycle having 1 to 3 heteroatoms selected from the group consisting of O, N or S in any combination; and wherein $R^{18}$ and $R^{19}$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, or a salt of $C_1$–$C_6$ sulfoalkyl, wherein the alkyl portions are optionally substituted by amino, hydroxy, carboxylic acid, a salt of carboxylic acid, or a carboxylic acid ester of a $C_1$–$C_6$ alkyl; or a covalent linkage L; or one or more of $R^{18}$ and $R^{19}$ is a Q moiety; or $R^{18}$ taken in combination with $R^{19}$ forms a saturated 5- or 6-membered heterocycle that is a piperidine, or a pyrrolidine that is optionally fused to a Q moiety, and optionally further substituted by methyl, carboxylic acid, a salt of carboxylic acid, a carboxylic acid ester of a $C_1$–$C_6$ alkyl; or a covalent linkage L;

or $R^{18}$ in combination with $R^4$, or $R^{19}$ in combination with $R^5$, or both, form a 5- or 6-membered ring that is saturated or unsaturated, and is optionally substituted by one or more $C_1$–$C_6$ alkyls or —$CH_2SO_3X$ moieties;

$R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino; or $C_1$–$C_{18}$ alkyl, $C_1$–$C_{18}$ alkoxy, $C_1$–$C^{18}$ alkylthio, $C_1$–$C_{18}$ alkanoylamino, $C_1$–$C_{18}$ alkylaminocarbonyl, $C_2$–$C_{36}$ dialkylaminocarbonyl, $C_1$–$C_{18}$ alkyloxycarbonyl, or $C_6$–$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alcohol, —$SO_3X$, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, or a salt of carboxylic acid; or one of $R^{12}$, $R^{13}$, $R^{14}$, $R^{15}$ and $R^{16}$ is a covalent linkage L;

provided that at least one of $R^8$, $R^9$, $R^{18}$, and $R^{19}$ is, or is fused to, a Q moiety; and further provided that at least one of $R^8$, $R^9$, $R^{12}$, $R^{13}$, $R^{14}$, $R^{15}$, $R^{16}$, $R^{18}$, or $R^{19}$ is a covalent linkage to said oligonucleotide, L, wherein L is a single covalent bond, or a linear or branched, cyclic or heterocyclic, saturated or unsaturated covalent linkage having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds.

54. A kit, as claimed in claim 53, wherein each Q moiety is a phenyl or substituted phenyl; and $R^{12}$ is the covalent linkage L; wherein L is bound to the oligonucleotide at the 5'-terminus, a base, a sugar, or a phosphate.

55. A kit, as claimed in claim 50, wherein the covalently bound quenching moiety is bound to the oligonucleotide at one or more purine or pyrimidine bases through an amide, ester, ether or thioether bond, or a transition metal complex.

56. A kit, as claimed in claim 50, wherein the covalently bound quenching moiety is bound to the oligonucleotide at the 5'-terminus.

57. A kit, as claimed in claim 50, wherein said nucleic acid stain is an unsymmetrical cyanine dye or a dimer of an unsymmetrical cyanine dye.

58. A method, as claimed in claim 5, wherein said nucleic acid stain is a phenanthridinium dye, an acridine dye, an indole dye, an imidazole dye, a cyanine dye, or a homo- or heterodimer thereof; and said quenching moiety is a xanthene dye, a phenoxazine dye, a triarylmethane dye, or an azo dye.

59. A method, as claimed in claim 6, wherein said nucleic acid stain is an unsymmetrical cyanine dye or a dimer of an unsymmetrical cyanine dye and said quenching moiety is a xanthene dye.

60. A method, as claimed in claim 10, wherein said nucleic acid stain is an unsymmetrical cyanine dye or a dimer of an unsymmetrical cyanine dye.

61. A method, as claimed in claim 19, wherein said nucleic acid stain is an unsymmetrical cyanine dye or a dimer of an unsymmetrical cyanine dye.

62. A method, as claimed in claim 27, wherein said nucleic acid stain is an unsymmetrical cyanine dye or a dimer of an unsymmetrical cyanine dye, and wherein said luminescence response of the mixrure is used to determine presence or activity of the elongation enzyme, or extent or rate of elongdtion.

63. A method, as claimed in claim 28, wherein said nucleic acid stain is an unsymmetrical cyanine dye or a dimer of an unsymmetrical cyanine dye and said quenching moiety is an N-aryl rhodamine dye.

64. A kit, as claimed in claim 54, wherein said nucleic acid stain is an unsymmetrical cyanine dye or a dimer of an unsymmetrical cyanine dye.

* * * * *